(12) United States Patent
Calleja et al.

(10) Patent No.: US 8,066,996 B2
(45) Date of Patent: Nov. 29, 2011

(54) ANTI-CCR7 RECEPTOR ANTIBODIES FOR THE TREATMENT OF CANCER

(75) Inventors: Cecilia Munoz Calleja, Madrid (ES); Manuel Jesus Alfonso Perez, Salamanca (ES); Sonia Lopez Giral, Madrid (ES)

(73) Assignee: Universidad Autonoma de Madrid, Madrid (ES)

( * ) Notice: Subject to any disclaimer, the term of this patent is extended or adjusted under 35 U.S.C. 154(b) by 444 days.

(21) Appl. No.: 11/994,833

(22) PCT Filed: Jul. 5, 2006

(86) PCT No.: PCT/EP2006/006556
§ 371 (c)(1),
(2), (4) Date: Aug. 20, 2008

(87) PCT Pub. No.: WO2007/003426
PCT Pub. Date: Jan. 11, 2007

(65) Prior Publication Data
US 2009/0123483 A1    May 14, 2009

(30) Foreign Application Priority Data

Jul. 6, 2005   (WO) ................ PCT/EP2005/007371

(51) Int. Cl.
*A61K 39/395* (2006.01)
(52) U.S. Cl. .................. 424/138.1; 424/130.1
(58) Field of Classification Search .......... None
See application file for complete search history.

(56) References Cited

U.S. PATENT DOCUMENTS

2004/0185507 A1 * 9/2004 Giles-Komar et al. ........ 435/7.2

FOREIGN PATENT DOCUMENTS

EP        1 255 112 A2    11/2002
WO    2004104574 A2    12/2004

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Alfonso-Perez, Manuel, et al., "Anti-CCR7 monoclonal antibodies as a novel tool for the treatment of chronic lymphocyte leukemia", "Journal of Leukocyte Biology", Jun. 2006, pp. 1157-1165, vol. 79, No. 6.
Corcione, Anna, et al., "CCL19 and CXCL12 trigger in vitro chemotaxis of human mantle cell lymphoma B cells", "Clinical Cancer Research", Feb. 1, 2004, pp. 964-971, vol. 10, No. 3.
Ghobrial, Irene M., et al., "Expression of the chemokine receptors CXCR4 and CCR7 and disease progression in B-cell chronic lymphocytic leukemia . . . ", "May Clinic Proceedings", Mar. 2004, pp. 318-325, vol. 79, No. 3.
Lopez-Giral, Sonia, et al., "Chemokine receptors that mediate B cell homing to secondary lymphoid tissues are highly expressed in B cell chronic . . . ", "Journal of Leukocyte Biology", Aug. 2004, pp. 462-471, vol. 76, No. 2.
Till, Kathleen J., et al., "The chemokine receptor CCR7 and alpha-4 integrin are important for migration of chronic lymphocytic leukemia cells . . . ", "Blood", Apr. 15, 2002, pp. 2977-2984, vol. 99, No. 8.
Cignetti, Alessandro, et al., "Chemokine receptor expression in acute myeloid leukemia cells (Abstract)", "Blood", Nov. 16, 2000, p. 116a, vol. 11, No. 1.

* cited by examiner

*Primary Examiner* — Sheela J Huff
(74) *Attorney, Agent, or Firm* — Steven J. Hulquist; Kelly K. Reynolds; Hulquist IP

(57) ABSTRACT

Antibodies, or antigen-binding fragment thereof, which bind to a CCR7 receptor are capable of selectively killing, impairing migration and/or blocking dissemination of tumor cells expressing a CCR7 receptor. Use of said antibodies for killing or for inducing apoptosis of said tumor is disclosed, thus providing an alternative therapy for treatment of cancer which tumor cells express a CCR7 receptor.

6 Claims, 7 Drawing Sheets

ANTI-CCR7 RECEPTOR ANTIBODIES FOR THE TREATMENT OF CANCER

CROSS REFERENCE TO RELATED APPLICATIONS

This application is filed under the provisions under the provisions of 35 USC 371 based on International Application PCT/EP2006/006556 filed Jul. 5, 2006, claiming priority of International Application PCT/EP2005/007371 filed Jul. 6, 2005. The disclosures of such international patent applications are hereby incorporated herein by reference, in their respective entireties, for all purposes.

FIELD OF INVENTION

The present invention relates, in general, to the treatment of cancer. More specifically, the invention relates to the treatment of cancers which tumour cells are cells expressing a CCR7 receptor by using antibodies to a CCR7 receptor which are capable of selectively killing, impairing migration and/or blocking dissemination of said tumour cells.

BACKGROUND OF THE INVENTION

Cancer is a group of diseases characterized by uncontrolled cell division (or by an increase of survival or apoptosis resistance) and by the ability of said cells to invade other neighbouring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis.

There are several types of cancers that can be classified by the type of cell in which it originates and by the location of the cell, i.e., carcinomas, which arise from the cells that cover external and internal body surface, e.g. skin, digestive tract or gland; leukaemia, which starts in blood-forming tissue such as the bone marrow, and causes large numbers of abnormal blood cells to be produced and enter into the bloodstream; Lymphoma, which is a cancer originating in lymph nodes and tissues of the body's immune system; melanoma, which arises in melanocytes; sarcoma, which begins in the connective tissue of bone or muscle; and teratoma, which begins within germ cells.

Cancer can be treated by surgery, chemotherapy, radiation therapy, immunotherapy or other methods. The choice of therapy depends upon the location and grade of the tumour and the stage of the disease.

A significant problem to address in tumour treatment regimens is the desire for a "total cell kill". This means that the more effective treatment regimens come closer to a total cell kill of all so-called "clonogenic" malignant cells, i.e., cells that have the ability to grow uncontrolled and lead to tumour mass formation that might be removed by the therapy.

Another tumour treatment strategy is the use of an "immunotoxin", in which an anti-tumour cell antibody is used to deliver a toxin to the tumour cells. However, in common with the chemotherapeutic approaches described above, immunotoxin therapy also suffers from significant drawbacks. For example, antigen-negative or antigen-deficient cells can survive and repopulate the tumour or lead to further metastases.

Even if a primary cancer is completely eliminated, a malignant tumour will often be metastatic. The formation of metastases of malignant tumours, initiated from a primary tumour at more or less remote locations of the body, is one of the most serious effects of cancer and one for which a satisfactory treatment protocol is currently unavailable. The currently available methods of cancer therapy have either been of limited success in preventing metastasis or give rise to serious and undesirable side effects.

Although the specific delivery of therapeutic agents, such as anti-cellular agents, toxins and coagulation factors, to tumour mass represents a significant advance in cancer treatment protocols, there is still room for additional or even alternative therapies. The identification of additional targets to allow specific tumour destruction in vivo would naturally be of benefit in expanding the number of targeting options.

The novel therapeutic strategies for treating cancer are now moving towards the use of specific treatments, including monoclonal antibodies (mAbs) against different antigens expressed by tumour cells, which may hopefully cure the disease.

Antigen selection in immunotherapy must take into account either the tumour specificity of the antigen, the antigenic density in the surface of the tumour cells and the antigen modulation or the internalization of the antigen-antibody complex, which can reduce the ability to produce cell death. In most cases, complement-dependent cell lysis (CDC) and antibody-dependent cell-mediated cytotoxicity (ADCC) are believed to be responsible for the clinical utility of the unconjugated mAbs, although the induction of apoptosis or cell cycle arrest could also play a substantial role in other cases.

Cancer cells may express certain molecular receptors. Different studies show that CC chemokine receptor 7 (CCR7) is expressed in different tumour cells, e.g., B-cell chronic lymphocytic leukaemia, non-Hodgkin lymphomas, breast cancer cells, malignant breast tumours, etc. Moreover, it appears that CCR7 receptor plays a role in lymph node metastasis of different cancers, e.g., gastric carcinoma, melanoma, non-small cell lung cancers, T-cell leukaemia cells, etc. Thus, said chemokine receptor (CCR7) can be selected as a possible target for mAb therapy in cancer.

CCR7 is a seven transmembrane-spanning domain G protein coupled receptor (GPCR). The family of G-protein coupled receptors (GPCRs) includes receptors for hormones, neurotransmitters, growth factors, and viruses [Yoshie O, Imai T, Nomiyama H. Novel lymphocyte-specific CC chemokines and their receptors. J Leukoc Biol. 1997; 62:634-644; Kim C H, Pelus L M, White J R, Applebaum E, Johanson K, Broxmeyer H E. CK beta-11/macrophage inflammatory protein-3 beta/EBI1-ligand chemokine is an efficacious chemoattractant for T and B cells. J Immunol. 1998; 160: 2418-2424; Dieu M C, Vanbervliet B, Vicari A, et al. Selective recruitment of immature and mature dendritic cells by distinct chemokines expressed in different anatomic sites. J Exp Med. 1998; 188:373-386; Willimann K, Legler D F, Loetscher M, et al. The chemokine SLC is expressed in T cell areas of lymph nodes and mucosal lymphoid tissues and attracts activated T cells via CCR7. Eur J Immunol. 1998; 28:2025-2034; Yoshida R, Nagira M, Imai T, et al. EBI1-ligand chemokine (ELC) attracts a broad spectrum of lymphocytes: activated T cells strongly up-regulate CCR7 and efficiently migrate toward ELC. Int Immunol. 1998; 10:901-910; Sallusto F, Schaerli P, Loetscher P, et al. Rapid and coordinated switch in chemokine receptor expression during dendritic cell maturation. Eur J Immunol. 1998; 28:2760-2769].

A particular case of a leukaemia which tumour cells express a CCR7 receptor is chronic lymphocytic leukaemia (CLL), the most common type of human adult leukaemia. Said leukaemia is a B cell leukaemia characterized by accumulation of a single clone of CD5+ B cells with a great resistance to undergo apoptosis due to deregulation of extracellular or intracellular signalling events implicated in programmed cell death. Despite its very low proliferation index, peripheral blood lymphocyte count reaches values greater than $5\times10^3/\mu L$ and leukaemic cells demonstrate a marked tendency to invade lymph nodes, spleen and bone marrow.

The treatment of CLL is based in the use of purine analogues, particularly fludarabine, alone or in association, as frontline regimen. To date, the only therapeutic combination resulting in a higher complete remission rate than that obtained with fludarabine, has been the use of rituximab, an anti-CD20 monoclonal antibody, in association with either fludarabine or fludarabine plus cyclophosphamide. Moreover, molecular remissions in bone marrow aspirates were achieved in CLL patients with the above combinations, raising the possibility that CLL may be potentially curable without stem cell transplantation. Obtaining the best initial response together with the elimination of CLL cells in the inoculum of the patients undergoing autologous transplantation constitute some of the main therapeutic challenges in CLL.

Mantle cell lymphoma (MCL) is an aggressive subtype of B-cell non-Hodgkin's lymphoma. The cells are characterized as CD20+ CD5+ CD23− with a t(11;14) and cyclin D1 overexpression. Patients are usually treated with either rituximab-CHOP (cyclophosphamida, hydroxyl daunorubicin, oncovin and prednisone) followed by stem cell transplantation or rituximab-HyperCVAD (cyclophosphamide, vincristine, adriamycin, and dexamethasone). However, MCL remains without cure in most cases, indicating a clear need for new treatment approaches.

It has been recently demonstrated that CLL patients presenting clinical lymphadenopathy have a higher in vitro migratory response of CLL cells to the ligands of CCR7, the homeostatic chemokines CCL19 (MIP3-β) and CCL21 (6Ckine). Therefore, blocking the entry of the CLL cells into secondary lymphoid tissue with anti-CCR7 mAbs could be another advantage. Also, in this sense, non-lymphoid tumours expressing ectopic CCR7 have the ability to metastasize into secondary lymphoid organs, whereas tumours lacking this molecule or other chemokine receptors involved in the homing to secondary lymphoid organs, present a minimal nodal dissemination.

Therefore, there is a need for additional cancer therapies, in particular, cancer and tumour cells expressing a CCR7 receptor. Advantageously, said therapy should allow specific tumour destruction in vivo by, for example, killing tumour cells, impairing migration and/or blocking dissemination of tumour cells.

SUMMARY OF THE INVENTION

The invention is based on the finding that CCR7 receptor is highly expressed in some tumour cells, it plays a main role in the entry of lymphoid cells into the secondary lymphoid organs, including lymph nodes (LN), and its expression is restricted to naïve T and B lymphocytes and mature dendritic cells (DC), thus, making said CCR7 receptor an interesting target for mAb therapy in cancer, particularly, in cancers which tumour cells express a CCR7 receptor. The inventors, surprisingly, have observed that mAbs to CCR7, i.e., antibodies which recognize an epitope in a CCR7 receptor and are capable of binding said CCR7 receptor, are capable in vitro of killing CLL and MCL cells, i.e., tumour cells expressing a CCR7 receptor whereas are not capable of substantially killing non-tumour cells expressing a CCR7 receptor such as T cell lymphocytes.

Therefore, the invention relates, in general, to the use of an antibody, or antigen-binding fragment thereof, which binds to a CCR7 receptor, for killing or for inducing apoptosis of tumour cells expressing a CCR7 receptor, in the manufacture of a pharmaceutical composition for treating cancer; in a particular embodiment, the cancer to be treated is characterized by tumour cells expressing a CCR7 receptor.

Thus, in an aspect, the invention relates to the use of an antibody, or antigen-binding fragment thereof, which binds to a CCR7 receptor, in the manufacture of a pharmaceutical composition for killing or inducing apoptosis of tumour cells expressing a CCR7 receptor.

In other aspect, the invention refers to a method for killing or for inducing apoptosis of tumour cells expressing a CCR7 receptor which comprises contacting said cells with an antibody, or antigen-binding fragment thereof, which binds to said CCR7 receptor.

In other aspect, the invention relates to a method for killing or for inducing apoptosis of tumour cells expressing a CCR7 receptor in a subject in need of said treatment which comprises administering to said subject a therapeutically effective amount of an antibody, or antigen-binding fragment thereof, which binds to said CCR7 receptor.

In other aspect, the invention relates to a method for impairing migration of tumour cells expressing a CCR7 receptor to secondary lymphoid tissue and/or for blocking dissemination of tumour cells into secondary lymphoid tissue which comprises contacting said tumour cells with an antibody, or antigen-binding fragment thereof, which binds to a CCR7 receptor.

In other aspect, the invention relates to a method for impairing migration of tumour cells expressing a CCR7 receptor to secondary lymphoid tissue and/or for blocking dissemination of tumour cells into secondary lymphoid tissue in a subject in need of said treatment which comprises administering to said subject a therapeutically effective amount of an antibody, or antigen-binding fragment thereof, which binds to a CCR7 receptor.

In other aspect, the invention refers to a method for identifying a compound for killing or for inducing apoptosis of tumour cells expressing a CCR7 receptor which comprises
a) contacting a cell expressing a CCR7 receptor with a candidate compound coupled to an anti-CCR7 antibody or a fragment thereof, and
b) determining whether said candidate compound kills said cells expressing a CCR7 receptor,
wherein a compound that kills said cell expressing a CCR7 receptor, is a compound potentially useful for killing or for inducing apoptosis of tumour cells expressing a CCR7 receptor.

µg/mL), an IgM mAb (clone 2H4) and an IgG2a mAb (clone 150503), or with CCL19 (1 µg/mL), one of the physiological ligands of CCR7, as positive control. Then, CCR7 MFI was determined by FCM in electronically gated CD19+CD5+ CLL cells. Lines represent the expression of CCR7 relative to the basal CCR7 MFI. A representative case is shown.

Figure 2:
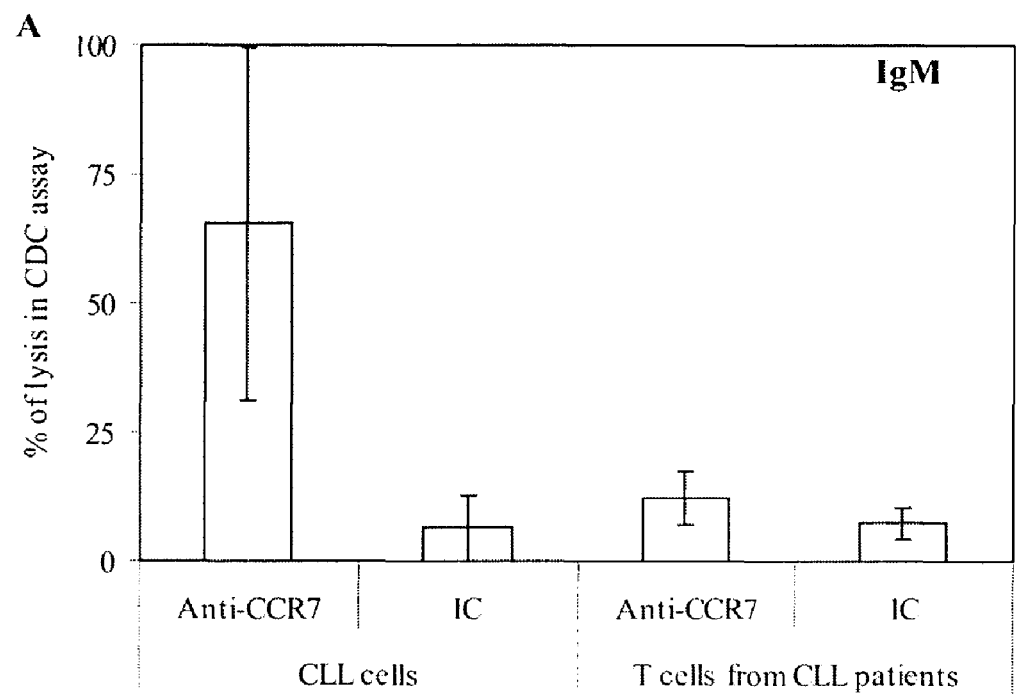
Figure 2:
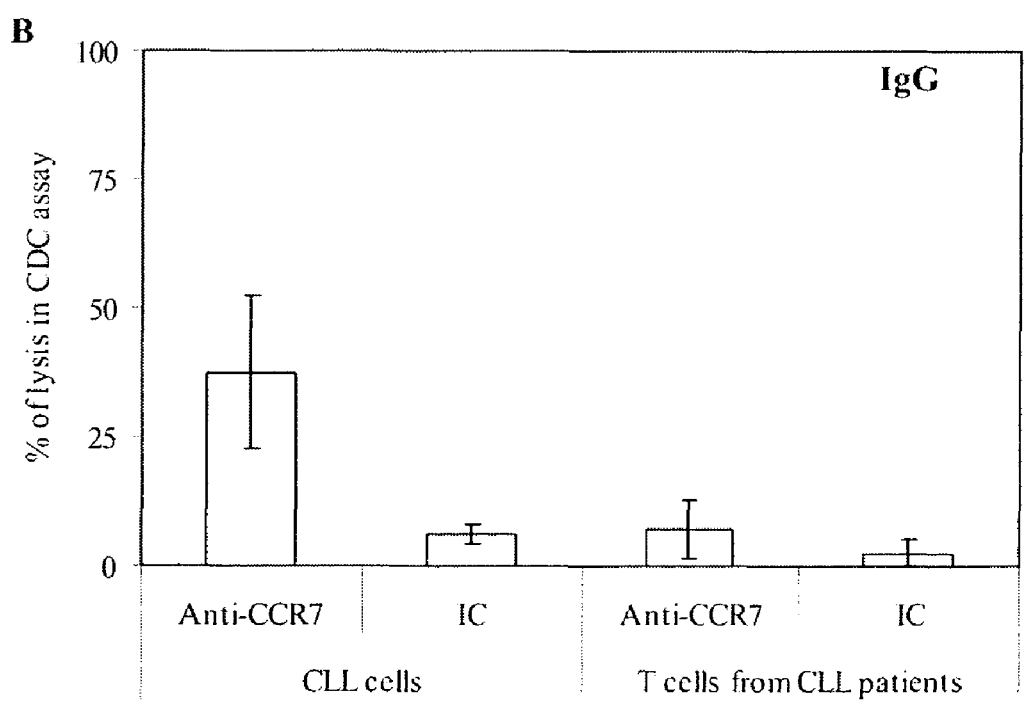

FIG. 2 shows that both anti-CCR7 mAbs mediate strong and specific complement-dependent cell lysis (CDC) of CLL cells. PBMC from CLL patients were incubated with anti-CCR7 mAbs or their respective isotype controls (IC) and then exposed to rabbit complement for an hour. Cell lysis was determined by 7-AAD incorporation and FCM analysis in electronically gated CLL cells and normal T cells. Bars represent mean±SD of 11 cases. (A) Anti-CCR7 IgM mAb (2 µg/mL), (B) Anti-CCR7 IgG mAb (2 µg/mL).

Figure 3:
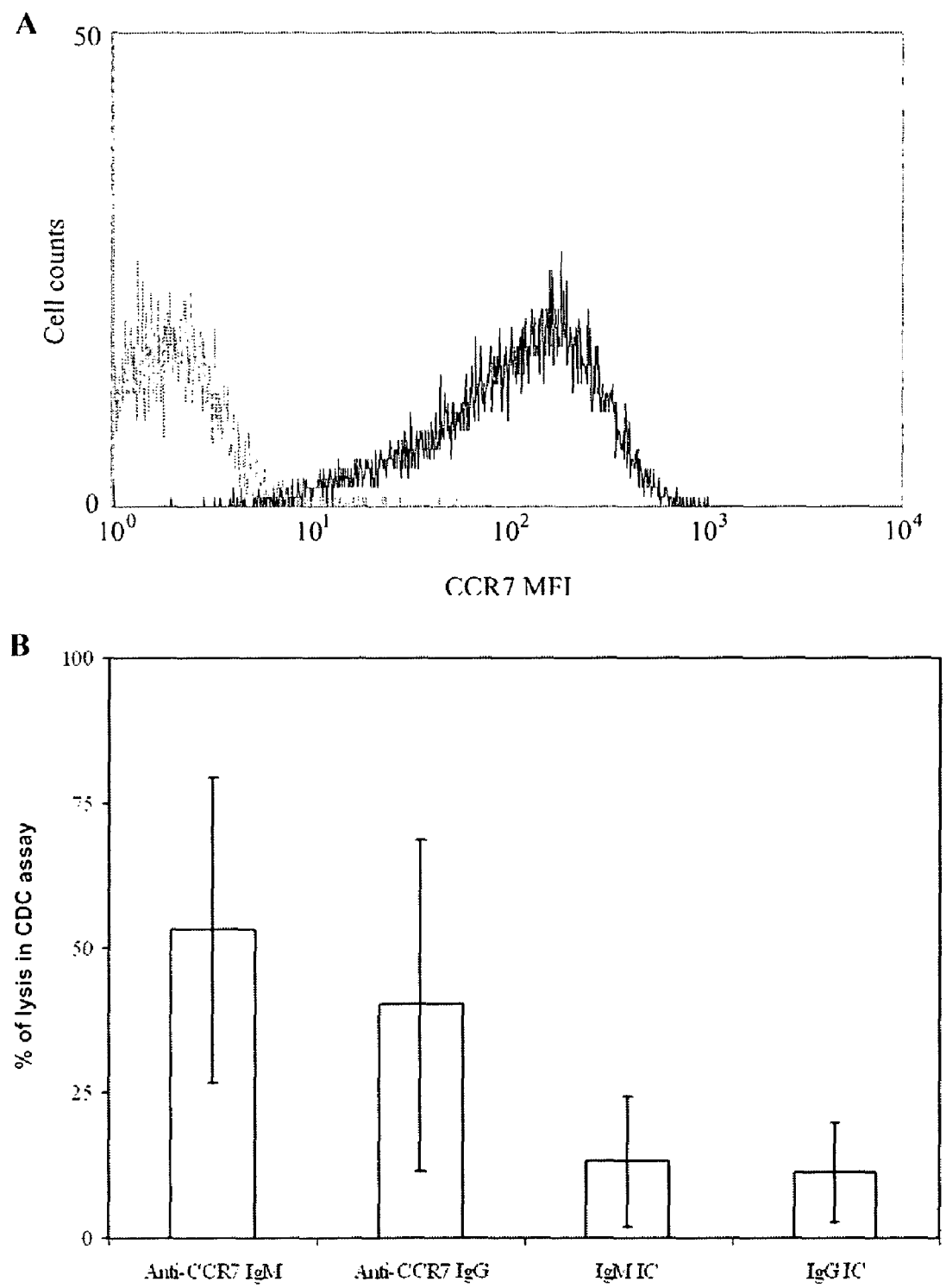

FIG. 3A shows the surface expression of CCR7 (black line) in tumor cells from a representative mantle cell lymphoma cell (MCL) patient, measured by flow cytometry including the corresponding IC (grey line) and FIG. 3B shows the CDC of MCL cells in the presence of anti-CCR7 mAbs or their respective IC. Mean±SD of 4 cases are shown.

Figure 4:
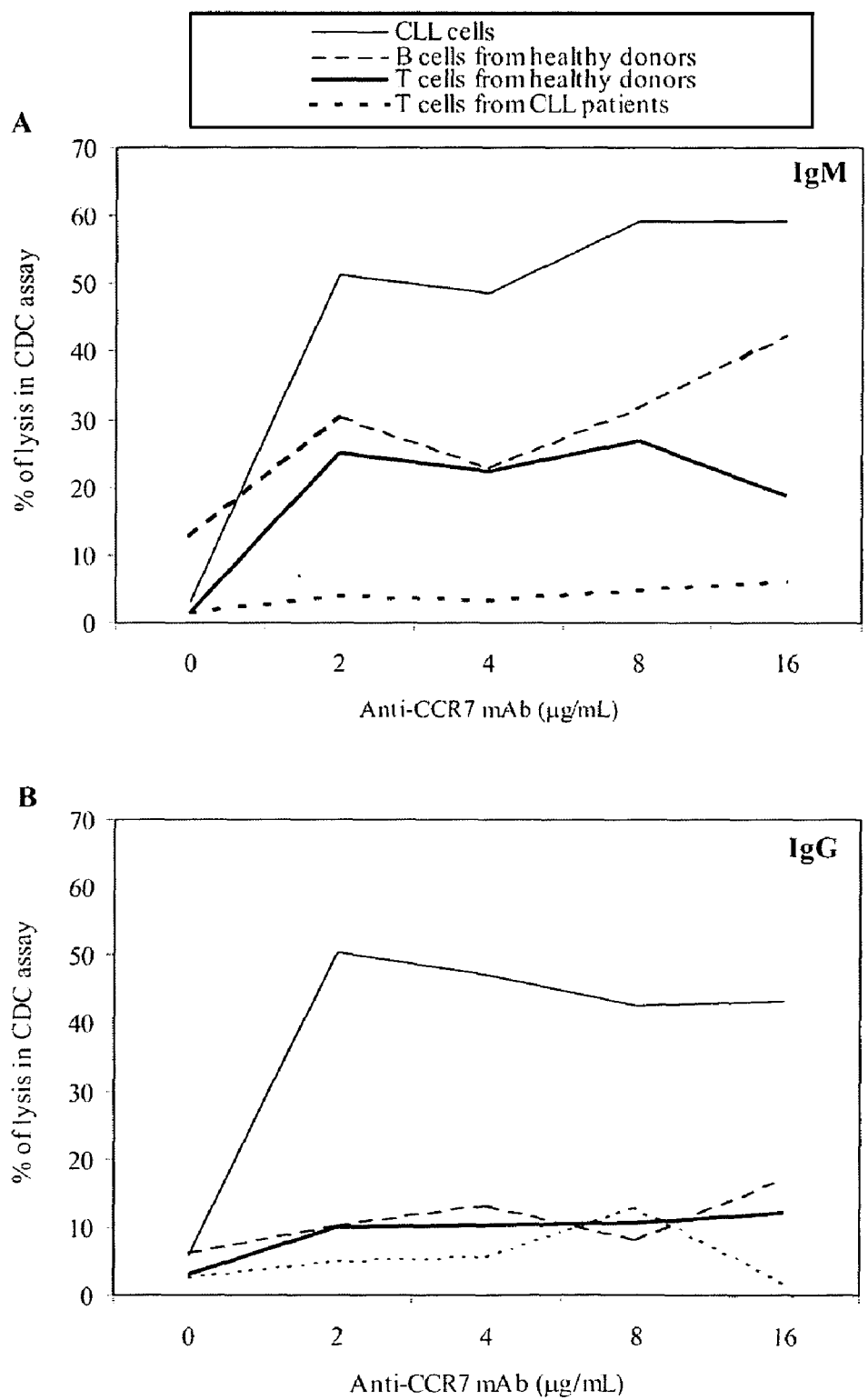

FIG. 4 describes dose-response curves for CDC. CDC assays with PBMC from CLL patients (n=5) and healthy donors (n=2) were performed with concentrations of the anti-CCR7 mAbs from 0.5 to 16 µg/mL. Percentage of cell lysis due to CDC was determined by 7-AAD incorporation and FCM analysis in electronically gated CLL cells, T lymphocytes from CLL patients and normal B and T cells from healthy donors. Lines represent mean of cell lysis. (A) Anti-CCR7 IgM mAb, (B) Anti-CCR7 IgG mAb.

Figure 5:
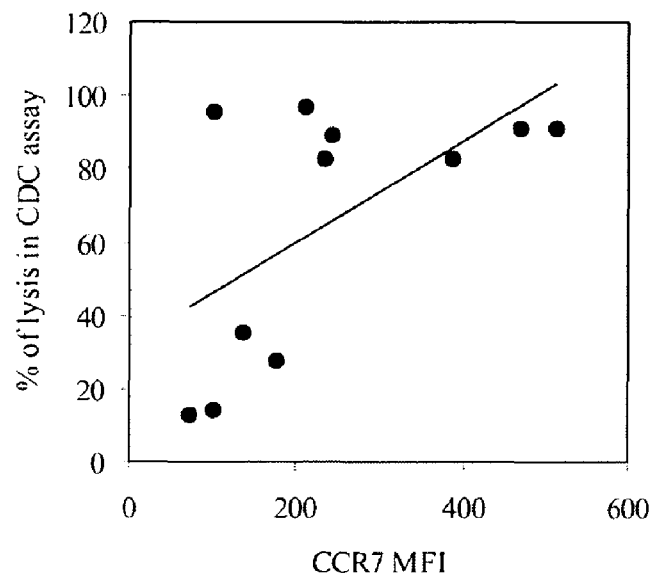

FIG. 5 shows that CDC potency correlates with CCR7 expression levels. CCR7 surface density of CLL cells correlated (r=0.602, P=0.025, n=11) with the percentage of lysis due to CDC mediated by 2 µg/mL of the anti-CCR7 IgM mAb after an hour of incubation with rabbit complement.

Figure 6:
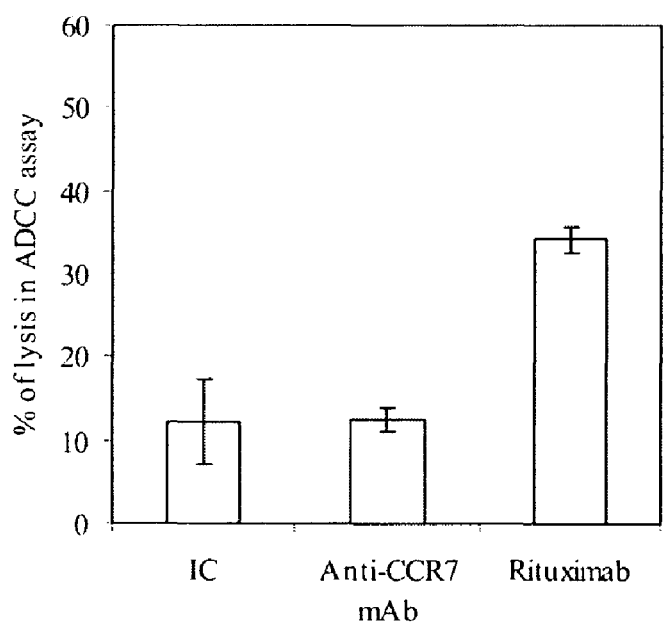

FIG. 6 shows that murine anti-CCR7 IgG mAb does not mediate ADCC of CLL cells. CLL cells previously incubated with either anti-CCR7 IgG mAb (2 µg/mL), the IC or rituximab (as positive control) were exposed to human natural killer (NK) cells for 4 hours. Then, dead cells were determined by 7-AAD incorporation and FCM analysis in electronically gated CLL cells. Bars show mean±SD of 6 experiments.

Figure 7:
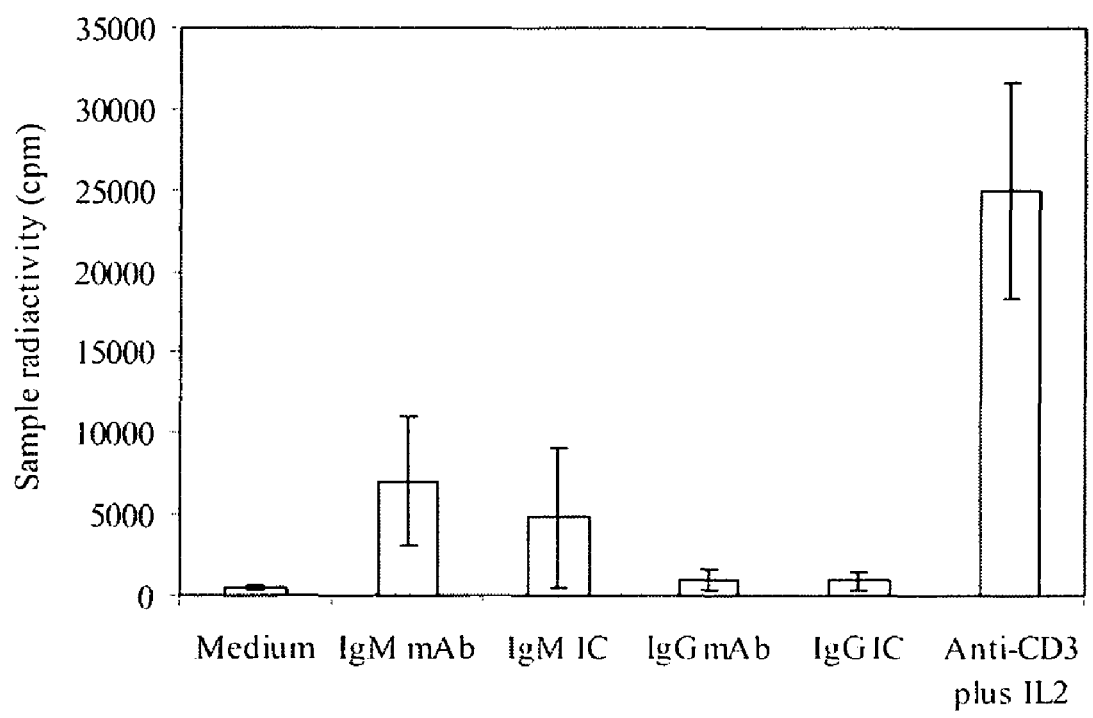

FIG. 7 shows that anti-CCR7 mAbs do not induce proliferation of lymphocytes. PBMC from healthy donors were cultured for 72 hours with the anti-CCR7 mAbs, ICs, anti-CD3 mAb plus IL2 or medium alone. DNA synthesis in the final 16 hours of culture was determined by [$^3$H]-thymidine incorporation. Bars represent mean±SD of 6 cases performed in triplicate.

Figure 8:
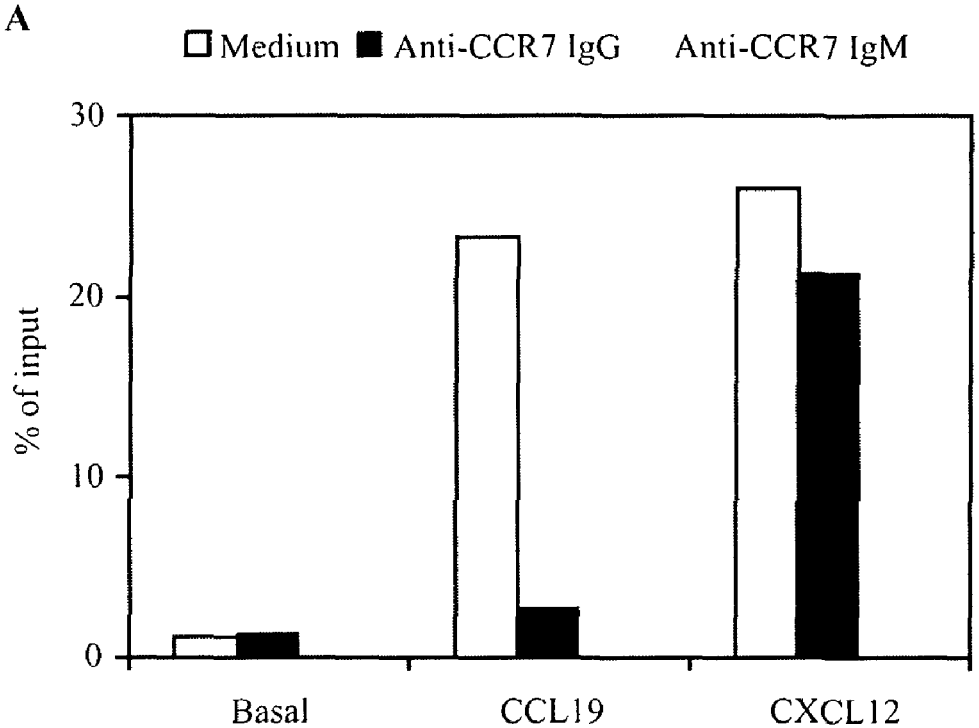
Figure 8:
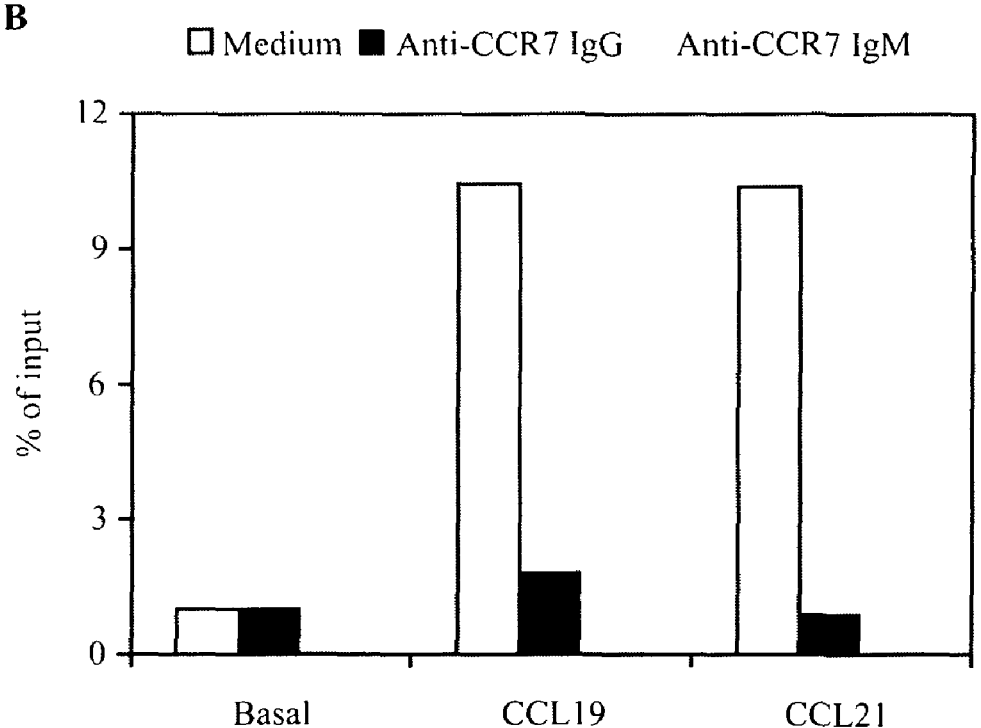

FIG. 8 shows that anti-CCR7 mAbs block the migration of CLL and MCL cells in response to CCL19 or CCL21. Chemotaxis assays were performed as described in Methods after preincubation of the cells for 30 minutes with 2 µg/mL of anti-CCR7 IgG (black bars), IgM (grey bars) mAbs or without mAbs (white bars). (A) Migration of CLL cells in response to CCL19 (1 µg/mL) was compared with basal migration and migration in the presence of CXCL12 (100 ng/mL), ligand of the chemokine receptor CXCR4, which was not affected by anti-CCR7 mAbs. A representative case is shown. (B) Migration of MCL cells in response to both ligands of CCR7, CCL19 (1 µg/mL) and CCL21 (1 µg/mL), was compared with basal migration. A representative case is shown.

DETAILED DESCRIPTION OF THE INVENTION

The present invention refers, in general, to the use of an antibody, or antigen-binding fragment thereof, which binds to a CCR7 receptor, in the manufacture of a pharmaceutical composition for treating cancer, in particular a cancer which tumour cells express a CCR7 receptor, by killing or inducing apoptosis of said tumour cells.

Thus, in an aspect, the invention refers to the use of an antibody, or antigen-binding fragment thereof, which binds to a CCR7 receptor in the manufacture of a pharmaceutical composition for killing or for inducing apoptosis of tumour cells expressing a CCR7 receptor.

Tumour cells of the cancer to be treated are tumour cells expressing a CCR7 receptor. Illustrative, non-limitative, examples of said type of cancer which tumour cells express a CCR7 receptor include chronic lymphocytic leukaemia (CLL), mantle cells lymphoma (MCL), follicular lymphoma, large B-cell lymphoma, AIDS-associated lymphoma, lymphoplasmacytic lymphoma, Burkitt lymphoma, B-cell acute lymphoblastic leukaemia, Hodgkin's disease, adult T-cell leukaemia/lymphoma, mycosis fungoides, blast crisis of chronic myeloproliferative syndromes, blast crisis of myelodysplastic syndromes, cancers such as breast cancer, non-small cell lung cancer, melanoma, gastric cancer or squamous cell carcinoma of the head and neck and colon carcinoma.

Tumour cells expressing a CCR7 receptor can be identified by conventional methods; for example, surface expression of CCR7 receptor can be analyzed by flow cytometry according to the method disclosed by López-Giral S. et al., (Journal of Leyukocyte Biology, Vol 76, August 2004, 462-471).

"Treating cancer", as used herein, means inhibiting or controlling the proliferation of tumour cells, said tumour cells being tumour cells expressing a CCR7 receptor. The term includes, among other things, killing said tumour cells, inducing apoptosis of said tumour cells impairing migration of said tumour cells to secondary lymphoid tissue and/or blocking dissemination of said tumour cells into secondary lymphoid tissue.

According to the invention, an antibody, or an antigen-binding fragment thereof, to, or specific for, a CCR7 receptor, i.e., which binds to a CCR7 receptor, sometimes referred herein as antibody of the invention, can be used for killing or for inducing apoptosis of tumour cells expressing a CCR7 receptor. Consequently, the antibody of the invention can be used in the manufacture of a pharmaceutical composition for killing or for inducing apoptosis of said tumour cells. As a consequence, the invention provides an alternative approach for treating cancer, particularly, a cancer which tumour cells express a CCR7 receptor.

The term "killing tumour cells", as used herein, refers to a mechanism of elimination of tumour cells, such as tumour cells expressing a CCR7 receptor, by the specific lysis of said cells. Said lysis or cytotoxicity is normally mediated by the recruitment of either complement proteins (CDC) or effector cells such as NK cells (ADCC) said proteins and NK cells being capable of specifically target and produce lysis, respectively, of said tumour cells after being treated with anti-CCR7 antibodies.

The term "inducing apoptosis of tumour cells", as used herein, refers to a mechanism by which tumour cells expressing a CCR7 receptor undergo apoptosis, i.e. programmed cell death, after being treated with anti-CCR7 antibodies.

The term "antibody of the invention", as used herein, refers to a gamma-globulin, or a fragment thereof, that exhibits a specific binding activity for a target molecule, namely, a CCR7 receptor (antigen). Thus, the antibody of the invention is capable of binding an epitope of CCR7; typically, at least 6, 8, 10, or 12, contiguous amino acids are required to form an epitope, however, epitopes which involve non-contiguous amino acids may require more, e.g., at least 15, 25, or 50 amino acid. The term "antibody of the invention" includes, for example, polyclonal antibodies, monoclonal antibodies, engineered or modified antibodies, chimeric antibodies, humanized antibodies, primatized antibodies, human antibodies, antibody fragments such as Fab, F(ab')$_2$, Fab', single chain Fv (scFv) fragments, diabodies bispecific antibodies and heteroconjugate antibodies. In addition, the antibody of the invention may be also conjugated to a further compound, such as a therapeutic agent, a toxin and the like. Such antibodies may be produced in a variety of ways, including hybridoma cultures, recombinant expression in bacteria or mammalian cell cultures, and recombinant expression in transgenic animals. Also antibodies can be produced by selecting a sequence from a library of sequences expressed in display systems such as filamentous phage, bacterial, yeast or ribosome. There is abundant guidance in the literature for selecting a particular production methodology, e.g., Chadd and Chamow, Curr. Opin. Biotechnol., 12:188-194 (2001). The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments, such as Fab and Fv fragments, as well as chimeric antibodies comprising components from different species. Antibody fragments of small size, such as Fab and Fv fragments, having no effector functions and limited pharmokinetic activity may be generated in a bacterial expression system. Single chain Fv fragments show low immunogenicity and are cleared rapidly from the blood.

The antibody of the invention, which specifically binds to an epitope of a CCR7 receptor, can be used therapeutically, as well as in immunochemical assays, such as immunofluorescence assays, flow cytometry, Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the CCR7 receptor immunogen.

The antibodies of the invention may be polyclonal antibodies. Such polyclonal antibodies can be produced in a mammal, such as a non-human mammal, for example, following one or more injections of an immunizing agent, and preferably, an adjuvant. Typically, the immunizing agent and/or adjuvant will be injected into the mammal by a series of subcutaneous or intraperitoneal injections. The immunizing agent may include a CCR7 receptor or a fragment thereof or a fusion protein thereof or a cell expressing a CCR7 receptor. Alternatively, a crude protein preparation which has been enriched for a CCR7 receptor or a fragment thereof can be used to generate antibodies. Such proteins, fragments or preparations are introduced into the non-human mammal in the presence of an appropriate adjuvant. Other form of administration of an immunogen is as a transmembrane protein in the surface of a cell (methods described in, e.g., Spiller et al. J. Immunol. Methods, 224: 51-60 (1999)). These cells can be everyone which naturally express the antigen in its cell membrane or in which this expression can be obtained after transfecting the cell with a DNA construct that contains among other DNA sequences those coding the antigen, those necessary for its sufficient expression in the cell. This approach is possible not only when the cell membrane is the natural site in which the antigen is expressed even the antigen once synthesized in the cell is directed at these location by a signal peptide which is added at the antigen coding sequence. If the serum contains polyclonal antibodies to undesired epitopes, the polyclonal antibodies can be purified by immunoaffinity chromatography.

Alternatively, said antibodies may be monoclonal antibodies. Monoclonal antibodies may be produced by hybridomas, wherein a mouse, hamster, or other appropriate host animal, is immunized with an immunizing agent to elicit lymphocytes that produce or are capable of producing antibodies that will specifically bind to the immunizing agent, e.g. Kohler and Milstein, Nature 256:495 (1975). The immunizing agent will typically include a CCR7 receptor or a fragment thereof or a fusion protein thereof and optionally a carrier or a crude protein preparation which has been enriched for a CCR7 receptor or a fragment thereof or a cell expressing a CCR7 receptor. Such proteins, fragments or preparations are introduced into the non-human mammal in the presence of an appropriate adjuvant. Other form of administration of an immunogen is as a transmembrane protein in the surface of a cell (methods described in, e.g., Spiller et al. J. Immunol. Methods, 224: 51-60 (1999)). These cells can be everyone which naturally express the antigen in its cell membrane or in which this expression can be obtained after transfecting the cell with a DNA construct that contains among other DNA sequences those coding the antigen, those necessary for its sufficient expression in the cell. This approach is possible not only when the cell membrane is the natural site in which the antigen is expressed even the antigen once synthesized in the cell is directed at these location by a signal peptide which is added at the antigen coding sequence. Alternatively, lymphocytes may be immunized in vitro. Generally, spleen cells or lymph node cells are used if non-human mammalian sources are desired, or peripheral blood lymphocytes ("PBLs") are used if cells of human origin are desired. The lymphocytes are fused with an immortalized cell line using a suitable fusing agent, such as polyethylene glycol, to produce a hybridoma cell. In general, immortalized cell lines are myeloma cells of rat, mouse, bovine or human origin. The hybridoma cells are cultured in a suitable culture medium that preferably contains one or more substances that inhibit the growth or survival of unfused, immortalized cells. Clones are isolated using the limiting dilution method and the culture medium (supernatant) in which the hybridoma cells are cultured can be assayed for the presence of monoclonal antibodies directed against CCR7 receptor by conventional techniques, such as by flow cytometry or by immunoprecipitation or by other in vitro binding assay, such as RIA or ELISA. Clones can also be cultured in vivo as ascites tumours in an animal.

Preferably, the binding specificity of monoclonal antibodies produced by a clone of hybridoma cells is determined by immunoprecipitation or by an in vitro binding assay, such as radioimmunoassay (RIA) or enzyme-linked immunoabsorbent assay (ELISA) or by immunofluorescent techniques such as fluorescence microscopy or flow cytometry.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be isolated from the CCR7 receptor-specific hybridoma cells and sequenced by using conventional procedures, e.g., by using oligonucleotide probes that are capable of binding specifically to genes encoding the heavy and light chains of murine antibodies. The hybridoma cells serve as a preferred source of such DNA. Once isolated, the DNA may be inserted into an expression vector, which is then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

Another method of generating specific antibodies, or antibody fragments, reactive against a target molecule is to screen expression libraries encoding immunoglobulin genes, or portions thereof, expressed in bacteria, yeast, filamentous phages, ribosomes or ribosomal subunits and other display systems. These methods normally use large libraries of antibody sequences or antibody fragment sequences obtained from diverse sources such healthy donors, patients or animals healthy or not. These sequences are cloned and expressed in an appropriate system and selected by its binding affinity for the antigen. Diverse approaches have been described to select antibodies or fragments with desired properties e.g. neutralizing, agonist, etc (Fernández, Curr. Op. Biotech., 15: 364-373 (2004); Schmidt, Eur. J. Biochem., 268: 1730-1738 (2001)). In an embodiment, antibodies and antibody fragments characteristic of hybridomas of the invention can also be produced by recombinant means by extracting messenger RNA, constructing a cDNA library, and selecting clones which encode segments of the antibody molecule.

Engineered or Modified Antibodies:

Numerous approaches make use of the molecular biology and genetic techniques such as the good knowledge of the genetics and structure of the immunoglobulins to construct different modifications of immunoglobulin molecule with the aim of improve its properties for clinical or other uses. Some of them tend to reduce the immunogenicity of the molecule in the species in which should be used and the resultant molecule has a sequence more homologous with this species. Various methods have been used to obtain mAbs of human origin avoiding the non ethically admissible proceedings in healthy humans. In other approaches the molecular weight and size are reduced e.g. in order to improve the distribution of the molecule into solid tumours. Other possibilities are conjugation in a molecule of binding domains for more than one target molecule (bispecific antibody or also triespecific, etc) or the conjugation of an antibody or a fragment with another molecule with the desired function e.g. a toxic agent, a hormone, growth factor, a immunomodulating agent (immunosuppressor or immunostimulator), an inhibitor of cell growth, etc. In general all the resultant molecules retain at least one variable domain of an antibody which gives the high specificity and affinity characteristic of the antigen-antibody binding. Some examples of these constructions are:

Chimeric Antibodies:

These refer to antibodies constructed with variable regions from an antibody of some species (normally a mammal in which the mAb was generated) and constant regions of other species (the one in which the chimeric antibody is to be used). The objective of such construction is to obtain an antibody with the original mAb but less immunogenic and better tolerated in the subject to be treated, with improved serum half-life and which can be recognized for effector immunological mechanisms i.e. complement, Fc receptor of cytotoxic cells or others specific receptor for imuglobulins that show species specificity.

Humanized Antibodies:

By "humanized antibody" is meant an antibody derived from a non-human antibody, typically a murine antibody, that retains the antigen-binding properties of the parent antibody, but which is less immunogenic in humans. This may be achieved by various methods, including (a) grafting the entire non-human variable domains onto human constant regions to generate chimeric antibodies; (b) grafting only the non-human complementarity determining regions (CDRs) into human framework and constant regions with or without retention of critical framework residues; and (c) transplanting the entire non-human variable domains, but "cloaking" them with a human-like section by replacement of surface residues.

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain.

Humanization can be essentially performed following the method of Winter and co-workers (Jones et al., Nature, 321: 522-525 (1986); Reichmann et al., Nature, 332:323-327 (1988); Verhoeyen et al., Science, 239:1534-1536 (1988)), by substituting hypervariable region sequences for the corresponding sequences of a human antibody. In practice, humanized antibodies are typically human antibodies in which some hypervariable region residues and possibly some framework region (FR) residues are substituted by residues from analogous sites in rodent antibodies. The choice of human variable domains, both light and heavy, to be used in making the humanized antibodies is very important to reduce immunogenicity retaining the specificity and affinity for the antigen. According to the so called "best-fit" method, the sequence of the variable domain of a rodent antibody is screened against the entire library of known human variable-domain sequences. The human sequence which is closest to that of the rodent is then accepted as the human framework region (FR) for the humanized antibody (Suns et al., J. Immunol., 151: 2296 (1993); Chothia et al., J. Mol. Biol, 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies are humanized, with retention of high affinity for the antigen and other favourable biological properties. To achieve this goal, according to a preferred method, humanized antibodies are prepared by a process of analysis of the parental sequences and various conceptual humanized products using three-dimensional models of the parental and humanized sequences.

Primatized Antibodies:

A further step in this approach, to make an antibody more similar to humans, is to prepare the so called primatized antibodies, i.e. a recombinant antibody which has been engineered to contain the variable heavy and light domains of a monkey (or other primate) antibody, in particular, a cynomolgus monkey antibody, and which contains human constant domain sequences, preferably the human immunoglobulin gamma 1 or gamma 4 constant domain (or PE variant). The preparation of such antibodies is described in Newman et al., Biotechnology, 10: 1458-1460 (1992); U.S. Pat. No. 5,658, 570 and U.S. Pat. No. 6,113,898. These antibodies have been reported to exhibit a high degree of homology to human antibodies, i.e., 85-98%, display human effector functions, have reduced immunogenicity, and may exhibit high affinity to human antigens. Another highly efficient means for generating recombinant antibodies is disclosed by Newman, Biotechnology, 10: 1455-1460 (1992).

Human Antibodies:

By "human antibody" is meant an antibody containing entirely human light and heavy chains as well as constant regions, produced by any of the known standard methods.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region PH gene in chimeric and germ-line mutant mice results in the complete inhibition of endogenous antibody production. Transfer of the human germ-line immunoglobulin gene array in such germ line mutant mice will result in the production of human antibodies after immunization. See, e.g., Jakobovits et al., Proc. Mad. Acad. Sci. USA, 90:255 1 (1993); Jakobovits et al., Nature, 362:255-258 (1993).

Alternatively, phage display technology (McCafferty et al., Nature 348:552-553 (1990)) can be used to produce human antibodies and antibody fragments in vitro, from immunoglobulin variable (V) domain gene repertoires from donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., Current Opinion in Structural Biology 3:564-57 1 (1993).

Human antibodies may also be generated by in vitro activated B cells or SCID mice with its immune system reconstituted with human cells.

Once a human antibody is obtained, its coding DNA sequences can be isolated, cloned and introduced into an appropriate expression system i.e. a cell line, preferably from a mammal, which subsequently express and liberate it into a culture media from which the antibody can be isolated.

Antibody Fragments:

An antibody fragment is a fragment of an antibody such as, for example, Fab, F(ab')$_2$, Fab' and scFv. Various techniques have been developed for the production of antibody fragments. Traditionally, these fragments were derived via proteolytic digestion of intact antibodies but more recently these fragments can be produced directly by recombinant host cells. In other embodiments, the antibody of choice is a single chain Fv (scFv) fragment which additionally may be monospecific or bispecific.

Papain digestion of antibodies produces two identical antigen-binding fragments, called "Fab" fragments, each with a single antigen-binding site, and a residual "Fe" fragment, which name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind the antigen, although with lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')Z antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Preferably, the Fv polypeptide further comprises a polypeptide linker between the VH and VL domains which enables the scFv to form the desired structure for antigen binding. For a review of scFv see Pluckthun in The Pharmacology of Monoclonal Antibodies, vol. 113, Rosenburg and Moore eds., Springer-Verlag, N.Y., pp. 269-315 (1994).

The term "diabodies" refers to small antibody fragments with two antigen-binding sites, those fragments comprising a heavy-chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

Functional fragments of antibodies which bind to a CCR7 receptor included within the present invention retain at least one binding function and/or modulation function of the full-length antibody from which they are derived. Preferred functional fragments retain an antigen-binding function of a corresponding full-length antibody (e.g., the ability to bind a mammalian CCR7 receptor). Particularly preferred functional fragments retain the ability to inhibit one or more functions characteristic of a mammalian CCR7 receptor, such as a binding activity, a signalling activity, and/or stimulation of a cellular response. For example, in one embodiment, a functional fragment can inhibit the interaction of CCR7 with one or more of its ligands and/or can inhibit one or more receptor-mediated functions.

Bispecific Antibodies:

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD 16) so as to focus cellular defense mechanisms to the B cell. Bispecific antibodies may also be used to localize cytotoxic agents to the B cell. These antibodies possess a B cell marker-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)₂ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CHI) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage.

Antibody Conjugation:

Cytotoxic chemotherapy or radiotherapy of cancer is limited by serious, sometimes life threatening, side effects that arise from toxicities to sensitive normal cells because the therapies are not selective for malignant cells. One strategy to avoid these problems is to couple the therapeutic agent to antibodies or other ligands that recognize tumour-associated antigens. This increases the exposure of the malignant cells, and reduces the exposure of normal cells, to the ligand-targeted therapeutics. See Allen, Nature, 2: 750-763 (2002).

The therapeutic agent can be an immunosuppressive agent i.e. a substance that act to suppress or mask the immune system of the mammal being treated herein. This would include substances that suppress cytokine production, down-regulate or suppress self-antigen expression, or mask the MHC antigens.

The therapeutic agent can also be a cytotoxic agent i.e. a substance that inhibits or prevents the function of cells and/or causes destruction of cells. The term is intended to include radioactive isotopes, chemotherapeutic agents i.e. chemical compounds useful in the treatment of cancer, and toxins such as small molecule toxins or enzymatically active toxins of bacterial, fungal, plant or animal origin, or fragments thereof.

The therapeutic agent can also be a cytokine, an hormone, growth factor, necrosis factor i.e. a protein or peptide released by one cell population which act on another cell as intercellular mediators or even in the same cell population. As used herein, the term cytokine includes proteins and peptides from natural sources or from recombinant cell culture and biologically active equivalents of the native sequence cytokines.

The therapeutic agent can also be a prodrug which refers to a precursor or derivative form of a pharmaceutically active substance that is less cytotoxic to tumour cells compared to the parent drug and is capable of being enzymatically activated or converted into the more active parent form.

Conjugates of an antibody and one or more small molecule toxins. In one preferred embodiment of the invention, the antagonist is conjugated to one or more toxin molecules. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes.

The present invention further contemplates antibody conjugated with a compound with nucleolytic activity (e.g. a ribonuclease or a DNA endonuclease such as a deoxyribonuclease; DNase) or other compound capable of damaging a cellular structure or organelle and therefore killing or diminishing the vitality of the cell.

The antibodies of the present invention may also be conjugated with a prodrug activating agent which converts a prodrug to an active anti-cancer drug. The agent component of such conjugates includes any agent capable of acting on a prodrug in such a way so as to covert it into its more active, cytotoxic form.

Alternatively, fusion proteins comprising at least the antigen binding region of an antagonist of the invention linked to at least a functionally active portion of an enzyme of the invention can be constructed using recombinant DNA techniques well known in the art (see, e.g., Neuberger et al., Nature, 312:604-608 (1984)).

Conjugates of the antibody and cytotoxic agent may be made using a variety of bifunctional protein coupling agents or linkers. The linker may be a "cleavable linker" facilitating release of the cytotoxic drug in the cell. For example, an acid-labile linker, peptidase-sensitive linker, dimethyl linker or disulfide-containing linker may be used.

Alternatively, a fusion protein comprising the antibody and cytotoxic agent may be made, e.g. by recombinant techniques or peptide synthesis.

Other Potentially Useful Modifications:

Amino acid sequence modification(s) of protein or peptide antagonists described herein are contemplated. For example, it may be desirable to improve the binding affinity and/or other biological properties of the antibody. Amino acid sequence variants of the antibody are prepared by introducing appropriate nucleotide changes into the antibody encoding nucleic acid, or by peptide synthesis. Such modifications include, for example, deletions from, and/or insertions into and/or substitutions of, residues within the amino acid sequences of the antagonist. Any combination of deletion, insertion, and substitution is made to achieve the final construct, provided that the final construct possesses the desired characteristics. The amino acid changes may also alter post-translational processes of the antagonist, such as changing the number or position of glycosylation sites.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antagonist with a N-terminal methionyl residue or the antagonist fused to a cytotoxic polypeptide. Other insertional variants of the antagonist molecule include the fusion to the N- or C-terminus of the antagonist of an enzyme, or a polypeptide which increases the serum half-life of the antagonist.

Another type of variant is an amino acid substitution variant. These variants have at least one amino acid residue in the antagonist molecule replaced by a different residue. The sites of greatest interest for substitutional mutagenesis of antibody antagonists include the hypervariable regions, but FR alterations are also contemplated.

Another type of amino acid variant of the antibody alters the original glycosylation pattern of the antagonist. By altering is meant deleting one or more carbohydrate moieties found in the antagonist, and/or adding one or more glycosylation sites that are not present in the antagonist. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of any of these tripeptide sequences in a polypeptide creates a potential glycosylation site. O-linked glycosylation refers to the attachment of one of the monosaccharides or monosaccharide derivatives N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antagonist.

It may be desirable to modify the antibodies used in the invention to improve effector function, e.g. so as to enhance ADCC and/or CDC of the antibody. This may be achieved by introducing one or more amino acid substitutions in an Fc region of an antibody.

Glycosyl groups added to the aminoacid backbone of glycoproteins e.g. antibodies are formed by several monosaccharides or monosaccharide derivatives in resulting in a composition which can be different in the same antibody produced in cell from different mammals or tissues. In addition, has been shown that different composition of glycosil groups can affect the potency in mediating antigen-dependent cell-mediated cyotoxicity (ADCC) and/or complement dependent cytotoxicity (CDC) of the antibody. Therefore it is possible to improve those properties by mean of studying the pattern of glycosilation of antibodies from different sources. An example of such approach is Niwa et al., Cancer Res. 2004 Mar. 15; 64(6):2127-33.

Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumour activity may also be prepared using heterobifunctional cross-linkers as described in Wolff et al. Cancer Research 53:2560-2565 (1993). Alternatively, an antibody which has dual Fc regions can be engineered and may thereby have enhanced complement lysis and ADCC capabilities. See Stevenson et al. Anti-Cancer Drug Design 3:2 19-230 (1989).

In order to increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgGl, IgG2, IgG3, or IgG4) that is responsible for increasing the in vivo serum half-life of the IgG molecule.

Preferably, the antibodies of the invention, e.g., monoclonal antibodies, Fv fragments, Fab fragments, or other binding compositions derived from monoclonal antibodies of the invention, have a high affinity to CCR7 receptor. The affinity of monoclonal antibodies and related molecules to CCR7 receptor may be measured by conventional techniques.

The affinity of an antibody for an antigen can be defined as the effectiveness of the antibody for binding such antigen. Antigen-antibody binding is a reversible binding and so when both molecules are in dilution in the same solution after sufficient time, this solution reaches an equilibrium in which the concentrations of antigen-antibody complex (AgAb), free antigen (Ag) and free antibody (Ab) are constant. Therefore the ratio [AgAb]/[Ag]*[Ab] is also a constant defined as association constant named Ka which can be used to compare the affinity of some antibodies for its respective epitope.

The common way to measure the affinity is to experimentally determine a binding curve. This involves measuring the amount of antibody-antigen complex as a function of the concentration of the free antigen. There are two common methods of performing this measurement: (i) the classical equilibrium dialysis using Scatchard analysis and (ii) the surface plasmon resonance method in which either antibody or antigen are bound to a conductive surface and binding of antigen or antibody respectively affects the electrical properties of this surface.

Often is only necessary to determine relative affinities of two or more mAbs that join the same epitope. In this case a competitive assay can be performed in which a serial dilution of one of the mAbs is incubated with a constant quantity of a ligand, and the second mAb labelled with any suitable tracer is then added. After binding of this mAb and washing the non-bounded antibodies, the concentration of second mAb is measured and plotted in relation to concentrations of the first mAb an analyzed with Scatchard method. An example is Tamura et al., J. Immunol. 163: 1432-1441 (2000).

In addition, the antibodies of the present invention can be useful for detecting a CCR7 receptor. Such detection methods are advantageously applied for diagnosis and/or prognosis of cancer which tumour cells are cells expressing a CCR7 receptor.

Further, the antibodies of the invention can be used to identify cells expressing a CCR7 receptor by standard techniques, such as immunofluorescence, flow cytometry, affinity chromatography or immunoprecipitation. For example, an antibody of the invention can facilitate the identification of a tumour cell expressing a CCR7 receptor. Moreover, the antibodies of the invention can be used to identify tumour cells expressing a CCR7 receptor in order to evaluate the level thereof in a specific tissue. Thus, antibodies of the invention can be used diagnostically to monitor levels of cells expressing a CCR7 receptor in tissue as part of a clinical testing procedure, e.g., to determine the efficacy of a given treatment regimen. Detection can be facilitated by coupling (i.e., physically linking) the antibody to a label group.

As described below, in a particular embodiment, the antibody of the invention can be used in combination with an additional therapeutically active compound such as a cytokine, an analgesic agent, an immunosuppressive agent and/or a chemotherapeutic agent. The combined administration includes co-administration, using separate formulations or a single pharmaceutical formulation, and consecutive administration in either order, wherein preferably there is a time period while both (or all) active agents simultaneously exert their biological activities.

In other aspect, the invention relates to a pharmaceutical composition, sometimes referred to as the pharmaceutical composition of the invention, comprising an antibody of the invention, i.e., an antibody, or antigen-binding fragment thereof, which binds to a CCR7 receptor, or a pharmaceutically derivative or prodrug thereof, together with a pharmaceutically acceptable carrier, adjuvant, or vehicle, for administration to a subject. Said pharmaceutical composition can be used for killing or for inducing apoptosis of tumour cells expressing a CCR7 receptor upon administration to a subject having a cancer. The term "subject", as used herein, refers to all animals classified as mammals and includes, but is not restricted to, domestic and farm animals, primates and humans. The subject is preferably a male or female human of any age or race.

The term "pharmaceutically acceptable carrier", as used herein, is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The antibodies of the invention may be in the same formulation or may be administered in different formulations. Administration can be concurrent or sequential, and may be effective in either order.

Supplementary active compounds can also be incorporated into the pharmaceutical composition of the invention. Thus, in a particular embodiment, the pharmaceutical composition of the invention may also contain more than one active compound as necessary for the particular indication being treated, preferably those with complementary activities that do not adversely affect each other. For example, it may be desirable to further provide a chemotherapeutic agent, a cytokine, an analgesic agent, or an immunosuppressive agent. The effective amount of such other active agents depends, among other things, on the amount of antibody of the invention present in the pharmaceutical composition, the type of disease or disorder or treatment, etc.

In an embodiment, the antibody of the invention is prepared with carriers that will protect said compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The administration route of the antibody (or fragment thereof) of the invention may be oral, parenteral, by inhalation or topical.

The term "parenteral" as used herein includes intravenous, intraperitoneal, intramuscular, subcutaneous, rectal or vaginal administration. The subcutaneous and intramuscular forms of parenteral administration are generally preferred.

By "inhalation" is meant intranasal and oral inhalation administration. Appropriate dosage forms for such administration, such as an aerosol formulation or a metered dose inhaler, may be prepared by conventional techniques.

Further, by "topical" administration is meant non-systemic administration and includes the application of an antibody of the invention externally to the epidermis, to the buccal cavity and instillation of such an antibody into the ear, eye and nose, and where it does not significantly enter the blood stream. By "systemic administration" is meant oral, intravenous, intraperitoneal and intramuscular administration. The amount of an antibody required for therapeutic or prophylactic effect will, of course, vary with the antibody chosen, the nature and severity of the condition being treated and the patient.

In addition, the antibody may suitably be administered by pulse infusion, e.g., with declining doses of the antibody. Preferably the dosing is given by injections, most preferably intravenous or subcutaneous injections, depending in part on whether the administration is brief or chronic.

Thus, in a particular embodiment, the pharmaceutical composition of the invention may be in an administration form suitable for oral administration, either solid or liquid. Suitable dose forms for oral administration may be tablets, capsules, syrops or solutions and may contain conventional excipients known in the art such as binding agents, for example syrup, acacia, gelatin, sorbitol, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrollidone, sodium starch glycollate or microcrystalline cellulose; or pharmaceutically acceptable wetting agents such as sodium lauryl sulfate. The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

In another embodiment, the pharmaceutical compositions of the invention may be adapted for parenteral administration, such as sterile solutions, suspensions or lyophilized products in the appropriate unit dosage form. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CremophorEM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, said pharmaceutical composition is administered via intravenous (IV) or subcutaneous (SC). Adequate excipients can be used, such as bulking agents, buffering agents or surfactants. The mentioned formulations will be prepared using standard methods such as those described or referred to in the Spanish and US Pharmacopoeias and similar reference texts.

It is especially advantageous to formulate the pharmaceutical compositions, namely, oral or parenteral compositions, in dosage unit form for ease administration and uniformity of dosage. Dosage unit form as used herein refers to physically discrete units suited as unitary dosages for the subject to be treated; each unit containing a predetermined quantity of active compound (antibody of the invention) calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally an effective administered amount of an antibody of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.001 to 1,000 mg/kg body weight/day, preferably about 0.01 to about 100 mg/kg body weight/day, most preferably from about 0.05 to 10 mg/kg body weight/day.

Aside from administration of antibodies to the patient, the present application contemplates administration of antibodies by gene therapy. W096/07321 relates the use of gene therapy to generate intracellular antibodies.

The pharmaceutical compositions can be included in a container, pack, or dispenser together with instructions for administration.

The antibodies and pharmaceutical compositions of this invention may be used with other drugs to provide a combination therapy. The other drugs may form part of the same composition, or be provided as a separate composition for administration at the same time or at different time.

The antibodies and pharmaceutical compositions of the present invention will be useful in the treatment of medical conditions, such as disorders or diseases associated with cancers, specially, for treating cancers said cancers being characterized by tumour cells expressing a CCR7 receptor, more specifically, for killing or inducing apoptosis of tumour cells expressing a CCR7 receptor. Illustrative, non-limitative, cancers which tumour cells express a CCR7 receptor susceptible of being treated according to the invention include chronic lymphocytic leukaemia (CLL), mantle cells lymphoma (MCL), follicular lymphoma, large B-cell lymphoma, AIDS-associated lymphoma, lymphoplasmacytic lymphoma, Burkitt lymphoma, B-cell acute lymphoblastic leukaemia, Hodgkin's disease, adult T-cell leukaemia/lymphoma, mycosis fungoides, blast crisis of chronic myeloproliferative syndromes, blast crisis of myelodysplastic syndromes, breast cancer, non-small cell lung cancer, melanoma, gastric cancer or squamous cell carcinoma of the head and neck and colon carcinoma. In a preferred embodiment, cancers susceptible of being treated according to the invention include breast cancer, non-small cell lung cancer, melanoma, gastric cancer or squamous cell carcinoma of the head and neck and colon carcinoma. In a most preferred embodiment, cancers susceptible of being treated according to the invention include follicular lymphoma, adult T-cell leukaemia/lymphoma, Burkitt lymphoma, blast crisis of chronic myeloproliferative syndromes and blast crisis of myelodysplastic syndromes. In a still most preferred embodiment, cancers to be treated according to the invention include CLL and MCL.

In a particular embodiment, the antibody of the invention may be combined with other treatments of the medical conditions described herein, e.g., chemotherapy, radiation therapy, immunotherapy, or surgical method, including alkylating agents, antimetabolites, antihormones, therapeutic for various symptoms, e.g., painkillers, diuretics, antidiuretics, antivirals, antibiotics, cytokines, nutritional supplements, anemia therapeutics, blood clotting therapeutics, bone therapeutics, psychiatric and psychological therapeutics, and the like.

Bone marrow or peripheral blood stem cells may be harvested from said patient subsequent to treatment with anti-CCR7 antibody in order to effect autologous bone marrow or stem cell transplantation.

It may also be useful to treat patients with cytokines in order to up-regulate the expression of CCR7 or other target protein on the surface of cancerous B cells prior to administration of an antibody of the invention. Cytokines may also be administered simultaneously with or prior to or subsequent to administration of the depleting antibody or radiolabeled antibody in order to stimulate immune effector functions.

In an embodiment, chemotherapeutic regimens may be used to supplement the therapies disclosed herein, and may be administered simultaneously with or sequentially in any order with administration of said radiolabeled antibody. The chemotherapy regimen may be selected from the group consisting of CHOP (cyclophosphamide, doxorubicin (also called hydroxyl daunorubicin), vincristine (also called oncovin) and prednisone), ICE (idarubicin, cytarabine and etoposide), Mitozantrone, Cytarabine, DVP (daunorubicin, vincristine and prednisone), ATRA (all-trans retinoic acid), Idarubicin, hoelzer chemotherapy regime, La chemotherapy regime, ABVD (bleomycin, dacarbazine, doxorubicin and vincristine), CEOP (cyclophosphamide, epirubicin, vincristine and prednisolone), 2-CdA (2-chlorodeoxyadenosine), FLAG & IDA (fludarabine, cytarabine, filgastrim and idarubicin), (with or without subsequent G-CSF (granulocyte-colony stimulating factor) treatment), VAD (vincristine, doxorubicine and dexamethasone), M & P (melphlan and prednisone), C (cyclophosphamide)-Weekly, ABCM (adriamycin, bleomycin, cyclophosphamide and mitomycin-C), MOPP (mechlorethamine, vincristine, prednisone and procarbazine) and DHAP (dexamethasone, cytarabine and cisplatin). A preferred chemotherapeutic regimen is CHOP.

Thus, in other aspect, the invention relates to a method for treating cancer specially a cancer which tumour cells express a CCR7 receptor which comprises administering to a subject in need of said treatment a therapeutically effective amount of an antibody of the invention, i.e., an antibody, or antigen-binding fragment thereof, which binds to the CCR7 receptor, or a pharmaceutical composition of the invention. In a particular embodiment, said cancer is a cancer characterized by tumour cells expressing a CCR7 receptor. Illustrative, non-limitative, cancers to be treated according to the invention include CLL, MCL, follicular lymphoma, large B-cell lymphoma, AIDS-associated lymphoma, lymphoplasmacytic lymphoma, Burkitt lymphoma, B-cell acute lymphoblastic leukaemia, Hodgkin's disease, adult T-cell leukaemia/lymphoma, mycosis fungoides, blast crisis of chronic myeloproliferative syndromes, blast crisis of myelodysplastic syndromes, breast cancer, non-small cell lung cancer, melanoma, gastric cancer or squamous cell carcinoma of the head and neck and colon carcinoma. In a preferred embodiment, cancers to be treated according to the invention include breast cancer, non-small cell lung cancer, melanoma, gastric cancer or squamous cell carcinoma of the head and neck and colon carcinoma. In a most preferred embodiment, cancers to be treated according to the invention include follicular lymphoma, adult T-cell leukaemia/lymphoma, Burkitt lymphoma, blast crisis of chronic myeloproliferative syndromes and blast crisis of myelodysplastic syndromes. In a still most preferred embodiment, cancers to be treated according to the invention include CLL and MCL.

In other aspect, the invention relates to a method for killing or for inducing apoptosis of tumour cells expressing a CCR7 receptor which comprises contacting said cells with an antibody of the invention, i.e., an antibody, or antigen-binding fragment thereof, which binds to a CCR7 receptor. In a particular embodiment, said tumour cells are tumour cells expressing a CCR7 receptor, such as CLL and MCL cells.

In other aspect, the invention relates to a method for killing or for inducing apoptosis of tumour cells expressing a CCR7 receptor in a subject in need of said treatment which comprises administering to said subject a therapeutically effective amount of an antibody of the invention, i.e., an antibody, or antigen-binding fragment thereof, which binds to said CCR7 receptor.

In other aspect, the invention relates to a method for impairing migration of tumour cells expressing a CCR7 receptor to secondary lymphoid tissue and/or for blocking dissemination of tumour cells into secondary lymphoid tissue which comprises contacting said tumour cells with an antibody of the invention, i.e. an antibody, or antigen-binding fragment thereof, which binds to a CCR7 receptor.

In other aspect, the invention relates to a method for impairing migration of tumour cells expressing a CCR7 receptor to secondary lymphoid tissue and/or for blocking dissemination of tumour cells into secondary lymphoid tissue in a subject in need of said treatment which comprises administering to said subject a therapeutically effective amount of an antibody, or antigen-binding fragment thereof, which binds to a CCR7 receptor.

Information concerning tumour cells expressing a CCR7 receptor susceptible of being treated with the methods of the invention, antibodies, administration regimens and dosages have been previously mentioned. In a particular embodiment, tumour cells expressing a CCR7 receptor susceptible of being treated with the above mentioned methods are CLL or MCL cells.

In all the cases, the expression "therapeutically effective amount" means an amount effective in treating cancer, as previously defined; said amount can be an amount sufficient to effect a desired response, or to ameliorate a symptom or sign, e.g., of metastasis or primary tumour progression, size, or growth. A therapeutically effective amount for a particular subject may vary depending on factors such as the condition being treated, the overall health of the subject, the method, route, and dose of administration and the severity of side effects. Preferably, the effect will result in a change in quantifying of at least about 10%, preferably at least 20%, 30%, 50%, 70%, or even 90% or more. When in combination, a therapeutically effective amount is in ratio to a combination of components and the effect is not limited to individual components alone.

A therapeutically effective amount will modulate the symptoms typically by at least about 10%; usually by at least about 20%; preferably at least about 30%; or more preferably at least about 50%. Alternatively, modulation of migration will mean that the migration or trafficking of various cell types is affected. Such will result in, e.g., statistically significant and quantifiable, changes in the numbers of cells being affected. This may be a decrease in the numbers of target cells being attracted within a time period or target area. Rate of primary tumour progression, size, dissemination or growth may also be monitored.

Any of the above mentioned therapeutic methods described above may be applied to any subject in need of such therapy, including, for example, mammals such as dogs, cats, cows, horses, rabbits, monkeys, and most preferably, humans.

In other aspect, the invention relates to a method for identifying a compound for killing or for inducing apoptosis of tumour cells expressing a CCR7 receptor which comprises
   a) contacting a cell expressing a CCR7 receptor with a candidate compound coupled to an anti-CCR7 antibody or a fragment thereof, and
   b) determining whether said candidate compound kills said cells expressing a CCR7 receptor,
   wherein a compound that kills said cell expressing a CCR7 receptor, is a compound potentially useful for killing or for inducing apoptosis of tumour cells.

Virtually, any cell expressing a CCR7 receptor, either a tumour or a non-tumour cell, can be used for working the above defined method. In a particular embodiment, said cell expressing a CCR7 receptor is a CLL of a MCL cell.

Death of the cells expressing a CCR7 receptor can be determined by any conventional method, for example, according to the method disclosed in the Example accompanying this description.

The following example serves to illustrate the invention.

Example

Antibodies to CCR7 as a Tool for Treating CLL

I. Material and Methods

Samples, Reagents and Flow Cytometry (FCM)

Peripheral blood samples from CLL (Chronic Lymphocytic Leukaemia) and MCL (mantle cell lymphoma) patients and healthy donors were obtained after informed consent. An initial immunophenotypic characterization of whole blood cells was performed by standard four-colour FCM with monoclonal antibodies (mAbs) directed against the following human surface antigens: CD45, CD19, kappa light chain, lambda light chain, CD20, CD23, CD5 and CD3 (all purchased from BD Biosciences, San Jose, Calif.). Samples with less than 60% of CLL or MCL cells on the mononuclear subpopulation were discarded. Analysis of CCR7 expression was subsequently performed on electronically gated tumour B cells or normal T and B lymphocytes. Phycoerythrin (PE)-conjugated mouse anti-human CCR7 was purchased from R&D Systems (McKinley Place, Minn.). In all cases appropriate isotype controls were included. Immunofluorescence staining was analyzed on a FACScalibur flow cytometer using CellQuest software (BD Biosciences).

Peripheral blood mononuclear cells (PBMC) were isolated by ficoll gradient centrifugation (Histopaque-1077, Sigma-Aldrich, Madrid, Spain).

Purified murine anti-human-CCR7 mAbs (hereinafter referred to as "anti-CCR7 mAbs") were obtained from BD Biosciences (150503 clone, IgG2a isotype) and R&D Systems (2H4 clone, IgM isotype). DNA dye 7-aminoactinomicin D (7-AAD) used in cell cycle analysis and cell viability assays was from BD Biosciences. Recombinant human chemokines CCL19 and CXCL12 were purchased from R&D Systems.

Receptor Endocytosis Assay

To study if the binding of the anti-CCR7 mAbs causes the internalization of the chemokine receptor (CCR7), $5 \times 10^5$ CLL cells were incubated with 2 µg/mL of the anti-CCR7 mAbs for different periods of time (ranging from 30 seconds to 1 hour) at 37° C. in 5% $CO_2$ atmosphere. CCL19, one of the physiological ligands of CCR7, which causes its endocytosis, was used as positive control. After the elimination of either bound mAb or CCL19 with an acidic wash (0.1 M glycine, 0.15 M NaCl, pH=2.5), CCR7 expression was determined on CLL cells by FCM analysis as indicated above.

Complement-Dependent Cytotoxicity (CDC)

Fifty µL of PBMC suspension containing $10^5$ cells were plated in a 96 round-bottom well plate together with the desired concentration, from 0.5 to 16 mg/mL, of purified anti-CCR7 mAbs or an isotype control (IC). After 30 minutes of incubation at 37° C., the cells were centrifuged and washed. Then, baby rabbit complement (Serotec, Oxford, UK) diluted at 25% in RPMI 1640 medium was added. After 1-2 hours at 37° C., the cells were stained with fluorescein-isothiocyanate (FITC)-conjugated anti-CD19, allophycocyanin (APC)-conjugated anti-CD5 mAb and 7-AAD. Both surface markers allow the discrimination by FCM of CLL cells, MCL cells and T-cells populations and 7-AAD was used as a viability exclusion dye. Percentage of non-viable cells was measured separately in each population and percentage of lysis with heat inactivated complement was used to calculate the specific lysis according to formula [1]

$$\text{Specific Lysis (\%)} = 100 \times \frac{(A - B)}{(100 - B)} \quad [1]$$

wherein
A: % dead cells with complement
B: % dead cells with inactivated complement Antibody-Dependent Cell-Mediated Cytotoxicity (ADCC)

Natural killer (NK) cells were isolated from PBMC obtained from buffy coats. A positive selection of the NK cells was performed by staining with PE-conjugated anti-CD56 mAb followed by magnetic cell sorting with anti-PE coupled micro-beads (Miltenyi Biotec GmbH, Bergisch-Gladbach, Germany). The purity of NK cells measured by FCM ranged from 95% to 98%. Anti-CCR7-dependent cell-mediated cytotoxicity was measured by FCM after 4 hours of incubation of CLL cells (target cells), with NK cells (as effector of cell lysis), at different effector-target (E/T) ratios between 5 and 40, in the presence or absence of the anti-CCR7 mAb or its isotype control. Then, the cells were stained with FITC-conjugated anti-CD19 mAb, PE-conjugated anti-CD56 mAb and 7-AAD to discriminate CLL cells and effector NK cells, and to analyze the viability of CLL cells. CLL cells incubated without NK cells were used as a control of spontaneous death and the specific lysis was calculated as in the CDC assay.

Chemotaxis Assay

The chemotaxis of CLL and MCL cells, previously incubated for 30 minutes with 2 µg/mL anti-CCR7 mAbs, in response to CCL29, CCL21 and CXCL12, the ligand of CXCR4, was assayed in Transwell cell culture chambers (6.5 mm diameter, 10 µm thickness, 5 µm diameter pore size, Costar, Cambridge, Mass.). For chemotaxis assay, $5 \times 10^5$ tumour cells suspended in 100 µl of RPMI 1640 with 0.5% BSA were added to the upper compartment of the chamber and chemokines were added to the lower well in 600 µl of the same medium at the optimal concentration (100 ng/mL for CXCL12 and 1 µg/mL for CCL19 and CCL21). Migration was allowed to proceed for 4 h at 37° C. in 5% $CO_2$ atmosphere. Migrated cells were recovered from the lower chamber, stained with an FITC-conjugated anti-CD19 mAb, and counted by FCM for 60 seconds after calibrating the flow rate with Trucount tubes (BD Biosciences). Events were analyzed within the gated population of B cells and compared with the numbers of cells counted in the initial suspension of cells to calculate the percentage of input (100× number of cells migrated/number of cells counted in the initial suspension). Each sample was measured in duplicate.

Apoptosis and Cell Cycle Analysis

In some experiments, anti-CCR7 mAbs were diluted at 2 µg/mL in 50 µL of culture suspension with $10^5$ CLL cells. In others, anti-CCR7 mAbs were attached to 96 flat-bottom well plates by overnight incubation in RPMI 1640. Then, the plate was washed and $10^5$ CLL cells were added. In both cases, the cells were incubated at 37° C. for a maximum of 48 hours. Cells were washed with cold phosphate buffered saline (PBS), stained with FITC-conjugated anti-CD19 mAb, resuspended in 0.5 mL of PBS and diluted in 5 mL of ice-cold 70% ethanol for an overnight fixation at −20° C. Next day, fixed cells were centrifuged, washed and stained with 20 µg/mL of 7-AAD for DNA content analysis. A minimum of 10,000 total events were acquired and analyzed using Cell-Quest Pro software (BD Biosciences). Briefly, CD19 positive events were gated and doublets were discarded using pulse-area and pulse-width of the 7-AAD fluorescence. Percentages of sub-$G_1$ peak as apoptotic cells were analyzed in the 7-AAD fluorescence histogram.

Proliferation Assay

PBMC were isolated from healthy donors and cultured for 72 hours in 96 well plates previously coated with both anti-CCR7 mAbs and their respective isotype controls. Positive controls such as anti-CD3 plus IL2 were also included. All measures were performed in triplicate. The cells were labeled with 1 µCi of [$^3$H]-thymidine (Amersham Biosciences GmbH, Freiburg, Germany) per well along the last 16 hours of the culture. Then the cells were harvested and subjected to scintillation counting.

Statistical Analysis

All statistical tests were performed in SPSS version 8.0. Wilcoxon and Kendall's W non-parametric tests and were used to compare the results of different treatments in most assays. For the [$^3$H]-thymidine proliferation assay an ANOVA was performed for comparison between groups. Pearson correlation coefficient was calculated to study the association between CCR7 mean fluorescence intensity (MFI) and percentage of lysis in CDC.

II. Results

Anti-CCR7 mAbs do not Induce Internalization of their Target

Figure 1:
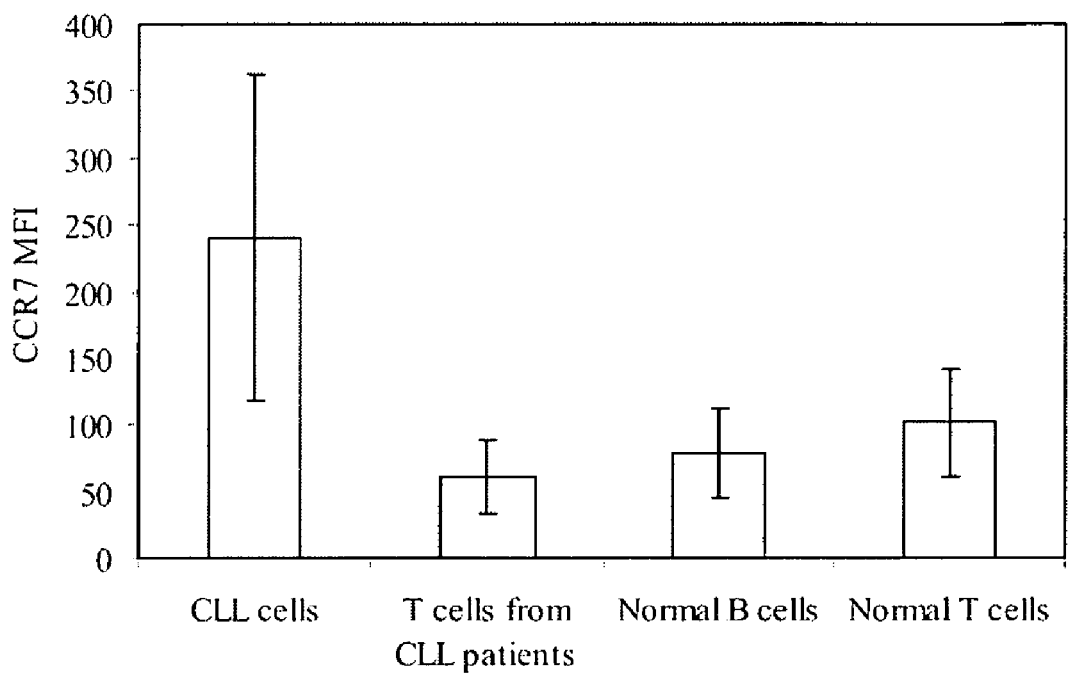
FIG. 1 shows in (A) that CCR7 surface expression is greater in tumour CLL cells than in normal B and T lymphocytes. Peripheral blood samples from 11 CLL patients and 6 healthy donors were analyzed by flow cytometry (FCM) to discriminate different lymphoid populations and their corresponding CCR7 surface density measured as mean fluorescence intensity (MFI). Bars represent mean±SD; and in (B) that anti-CCR7 mAbs do not cause endocytosis of the receptor. Peripheral blood mononuclear cells (PBMC) from CLL patients were incubated for different periods of time between 30 seconds and 60 minutes with the anti-CCR7 mAbs used (2
Figure 1:
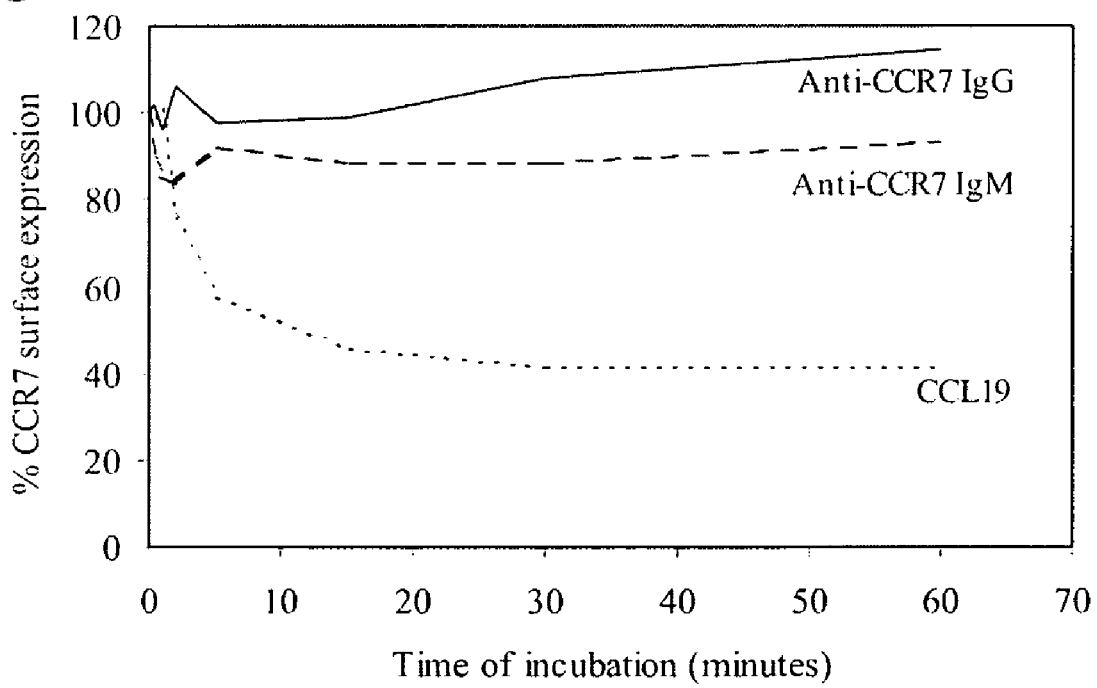

The use of therapeutical mAbs in their unconjugated form requires not only a high density of the target antigen, but also the presence of antigen-antibody complexes on the surface of the cells to activate complement or bind Fc receptors of cytotoxic cells, i.e., it is important that the binding of the mAb to the antigen does not induce its internalization because this could decrease the therapeutic effect of the mAb. In this regard, it has been suggested that antibody binding to some chemokine receptors can result in the endocytosis of the receptor followed by its proteolysis or re-expression after antibody degradation. Inventors analyzed if the binding of the mAbs to CCR7 produced its internalization in CLL cells. The expression of CCR7 on the surface of CLL cells was two to four-fold higher in CLL cells than in normal B or T cells (FIG. 1A) and did not decrease after their incubation with the anti-CCR7 mAbs for different times up to 60 minutes (FIG. 1B). Conversely, it decreased about 60% in the first 5 minutes of incubation with 1 micrograms/mL of CCL19 which served as positive control.

Anti-CCR7 mAbs Mediate Strong and Specific CDC of CLL and MCL Cells In Vitro

The cytotoxicity mediated by the recruitment of either complement proteins (CDC) or effector cells such as NK cells (ADCC) are the main mechanism of action proposed for the in vivo elimination of tumour cells by unconjugated therapeutic mAbs. Therefore, the potency of the anti-CCR7 mAbs in mediating CDC was tested with CLL and MCL samples from different patients. A very high proportion of CLL cells preincubated with the anti-CCR7 IgM mAb was killed after an hour of treatment with rabbit complement (FIG. 2A). Similarly, the anti-CCR7 mAb with IgG isotype also mediated a significant CDC (FIG. 2B).

Similarly to CLL, MCL cells also express significant levels of CCR7 (FIG. 3A) and CDC experiments showed that both anti-CCR7 mAbs efficaciously killed CCR7-positive MCL cells (FIG. 3B). No significant CDC was observed when irrelevant immunoglobulins of the same isotype were employed (FIGS. 2A, 2B and 3B).

Despite the comparatively lower efficacy of the anti-CCR7 mAb of the IgG isotype in causing CDC, kinetic assays demonstrated that its complement-activating capacity can be significantly increased by extending the time of incubation with the complement source (data not shown). This may be due to a slower activation of the complement cascade by mAbs with IgG2a isotype.

CCR7 is not restricted to CLL or MCL cells, being also expressed by certain normal lymphoid subpopulations, mainly naïve B and T lymphocytes, which could be susceptible to cytotoxicity mediated by anti-CCR7 mAbs. Interestingly, CDC mediated by anti-CCR7 mAbs was significantly higher (P=0.001 and P=0.016 for IgM and IgG mAbs, respectively) in CLL cells than in T cells from the same patients. Similarly, B and T lymphocytes from healthy donors were resistant to complement activity when treated in the same experimental conditions as above and even with higher doses of both anti-CCR7 mAbs as demonstrated dose-response assays (FIGS. 4A and 4B). This was particularly true with T cells from CLL patients which suffered almost no lysis (FIGS. 4A and 4B), probably due to the high and rapid complement consumption by the CLL cells presents in the sample. On the other hand, concentrations as low as 1 µg/mL of both anti-CCR7 mAbs were sufficient to mediate CDC of CLL cells (FIGS. 4A and 4B).

A possible explanation is the existence of a different sensitivity to CDC activity due to the much lower expression of CCR7 in normal T and B lymphocytes than in CLL cells (FIG. 1A). Indeed, the levels of expression of CCR7 in CLL cells significantly (r=0.602, P=0.025, n=11) correlated with the sensitivity to CDC of the different samples (FIG. 5), confirming the importance of the antigen density in the selection of a target for immunotherapy.

Moreover, differences in CDC activity did not seem to be related to a differential expression of complement regulatory proteins such as CD55 or CD59 as their levels of expression were very similar among different CLL samples and between CLL cells and T lymphocytes from these patients (data not shown).

In Vitro ADCC of CLL Cells

The other main mechanism mediating the beneficial effects of the therapeutic mAbs is the cytotoxicity mediated by cells (ADCC). Therefore, inventors tested the ability of NK cells to produce lysis of CLL cells previously treated with the anti-CCR7 IgG mAb. In 6 experiments performed with E/T ratios between 5 and 40, no significant ADCC was found in the presence of this anti-CCR7 mAb (mean lysis=13%±1, n=6) when compared with an irrelevant immunoglobulin with the same isotype (mean lysis=12%±5, n=6) (FIG. 6). This is probably related to the low affinity of the human Fc receptors for the murine mAbs. Conversely, rituximab, a well-known chimeric anti-CD20 mAb, IgG1 isotype, mediated ADCC against CLL cells with a mean lysis=34%±2 (n=6) (FIG. 6). ADCC in the presence of the anti-CCR7 IgM mAb was not tested since this isotype is not efficacious in mediating this kind of cytotoxicity.

Apoptosis and Proliferation in Response to Anti-CCR7 mAbs

Growing evidences suggest that a substantial portion of the beneficial responses to the therapeutic mAbs are due to direct effects on cell cycle or survival of the target cells. The effect of the anti-CCR7 mAbs on the apoptosis of CLL cells was studied by 7-AAD staining of the cellular DNA and sub-$G_1$ peak analysis. The rate of apoptosis of CLL cells treated for 24 hours with soluble anti-CCR7 IgM mAb was not significantly different from apoptosis of CLL cells treated with an IC (data not shown). Similarly, cross-linking of CCR7 by plate binding of anti-CCR7 mAbs up to 48 hours did not result in an induction of apoptosis (data not shown).

In order to study the proliferation of cells in response to anti-CCR7 mAbs, classical [$^3$H]-thymidine uptake proliferation assays were performed with PBMC from healthy donors, as CLL cells present a high spontaneous rate of apoptosis after 48-72 hours of incubation. These assays revealed a moderate increase in [$^3$H]-thymidine incorporation in cells after incubation with the anti-CCR7 mAb with IgM isotype which was not significantly different from the one obtained with an IgM IC. Conversely, neither the anti-CCR7 mAb with IgG isotype nor its IC induced proliferation (FIG. 7). As positive control, the PBMC proliferated in response to incubation with anti-CD3 mAb plus IL2.

Inhibition of the In Vitro Migration of CLL and MCL Cells by Anti-CCR7 mAbs

CCR7 plays a main role not only in physiological homing of naïve lymphocytes and mature dendritic cells, but also in the metastatic migration of tumour (cancer) cells expressing it and, particularly, CLL and MCL cells. Neutralizing the function of this chemokine receptor could be of interest in CLL and MCL patients in order to block the dissemination of these diseases to the lymphoid tissue. In this regard, inventors have assayed the ability of anti-CCR7 mAbs to neutralize the in vitro migration of CLL and MCL cells in response to CCL19 or CCL21. The anti-CCR7 mAb with IgG isotype was very effective in blocking the migration of these cells towards CCL19 or CC21, whereas the anti-CCR7 mAb with IgM isotype slightly decreased it (FIG. 8A-B).

In these assays, migration of CLL cells in response to CXCL12 (ligand of the chemokine receptor CXCR4) was not affected by either the two mAbs employed.

III. Discussion

Previous data from inventors showed that the levels of expression of the chemokine receptors CCR7, CXCR4 and CXCR5 on B-cell lymphoproliferative disorders are very heterogeneous depending on the histological subtype, and significantly related to lymph node (LN) involvement, since these molecules mediate the entry and positioning of lymphocytes into the secondary lymphoid tissue. The expression of CCR7 is especially high in CLL and mantle cells lymphoma, explaining the high tendency of these diseases to invade LNs. Similarly, recent studies have reported the expression of CCR7 on malignant cells from either other hematological malignancies like Hodgkin's disease, adult T-cell leukaemia/lymphoma and mycosis fungoides or non-hematologic solid tumours like breast cancer, non-small cell lung cancer, melanoma, gastric cancer, squamous cell carcinoma of the head and neck or colon carcinoma. Interestingly, this expression correlates, in all cases, with a characteristic pattern of migration and metastasis into the lymphoid tissue.

These data suggest the possibility of using CCR7, as therapeutical target in immunotherapy, not only due to their high density in certain malignant cells and to their restricted expression in normal tissues but also because of their crucial role in disease progression and pathogenicity.

CDC is accepted as the main mechanism of action of unconjugated therapeutic mAb when the target antigen is highly expressed, because CDC is believed to require about ten-fold more surface antigen density than ADCC. Therefore, inventors assayed the ability of anti-CCR7 mAbs to fix complement and mediate cytotoxicity against CLL cells, MCL cells and normal T lymphocytes from CLL patients. Their results show an important lysis of CLL and MCL cells due to complement fixation with little damage of T cells even under conditions of saturating concentrations of anti-CCR7 mAbs and complement. This could be due to the lower expression of CCR7 on normal T cells when compared to CLL cells. In this regard, inventors found a close correlation (p=0.025, r=0.602) between the CCR7 density on the surface of CLL cells and the percentage of lysed cells under the same experimental conditions. Importantly, these results suggest that treatment of CLL or MCL with anti-CCR7 mAbs, even at low concentrations, may result in an effective elimination of the tumour cells without lysing normal lymphocytes expressing the molecule (CCR7). It is possible to hypothesize that the secondary immunodeficiency due to the treatment with an anti-CCR7 mAb, would not be very important as CCR7-negative effector lymphocytes would remain undisturbed. The extrapolation of the immunological deficiencies that characterize the CCR7-deficient mice to CLL or MCL patients treated with anti-CCR7 mAbs is somehow difficult, as these individuals have already developed immunological memory that is absent in the knockout for CCR7.

Unlike the findings regarding CDC, the anti-CCR7 mAb with IgG isotype studied was not an activator of ADCC, probably due to its murine origin. Nevertheless, it is well known that molecular engineering techniques make possible the development of chimeric or humanized antibodies to improve clinical properties like the ability of mAb to mediate cell cytotoxicity through Fc receptors of monocytes, neutrophils and NK cells. In any case, the importance of ADCC in the immunotherapy for CLL is currently under discussion, due to the great expansion of malignant cells and functional defects in the T and NK cells of these patients. In this regard, several protocols have been recently published in order to expand and activate cytotoxic lymphocytes and NK cells from healthy donors or CLL patients to exploit this mechanism of action of the therapeutic mAbs.

Blocking the function of the target antigen constitutes another mechanism of action of therapeutic mAbs. In this invention, blocking anti-CCR7 mAbs may have the additional advantage of inhibiting the function of the probably main molecule involved in the nodal dissemination of lymphoid tumours and other non-hematological malignancies expressing it. In this regard, it is well known that neither rituximab nor alemtuzumab are very effective in reducing lymphadenopathies in CLL patients.

These results open a new therapeutic chance for those pathologies in which a blocking anti-CCR7 mAb could impair the migration to LN and thus block tumour dissemination in addition of killing cells by CDC or ADCC.

The invention claimed is:

1. A method for the treatment of a subject having a tumoral condition comprising the presence of tumor cells expressing a CCR7 receptor, said method comprising administering to said subject an antibody that binds to a CCR7 receptor in said tumor cells and is effective for killing said tumor cells expressing a CCR7 receptor.

2. The method according to claim 1, wherein said tumor cells are chronic lymphocytic leukemia (CLL) cells or Mantle Cell Lymphoma (MCL) cells.

3. The method according to claim 1, wherein the antibody that binds to a CCR7 receptor is used in combination with an additional therapeutically active compound.

4. A method for killing tumor cells expressing a CCR7 receptor which comprises contacting said cells with an antibody that binds to said CCR7 receptor.

5. A method for killing tumor cells expressing a CCR7 receptor in a subject in need of said treatment, which comprises administering to said subject a therapeutically effective amount of an antibody that binds to said CCR7 receptor.

6. The method according to claim 4, wherein said tumor cells are chronic lymphocytic leukemia (CLL) cells or Mantle Cell Lymphoma (MCL) cells.

* * * * *

UNITED STATES PATENT AND TRADEMARK OFFICE
CERTIFICATE OF CORRECTION

| | |
|---|---|
| PATENT NO. | : 8,066,996 B2 |
| APPLICATION NO. | : 11/994833 |
| DATED | : November 29, 2011 |
| INVENTOR(S) | : Cecilia Munoz Calleja |

Page 1 of 1

It is certified that error appears in the above-identified patent and that said Letters Patent is hereby corrected as shown below:

Cover page under "References Cited" and "Other Publications" the Ghobrial et al. reference journal name "May Clinic Proceedings" should be -- Mayo Clinic Proceedings --.

Column 11, line 59: "...'Fe' fragment..." should be -- Fc fragment --.

Column 17, line 1: "...an analyzed..." should be -- and analyzed --.

Signed and Sealed this
First Day of May, 2012

David J. Kappos
*Director of the United States Patent and Trademark Office*

UNITED STATES PATENT AND TRADEMARK OFFICE
CERTIFICATE OF CORRECTION

PATENT NO. : 8,066,996 B2  
APPLICATION NO. : 11/994833  
DATED : November 29, 2011  
INVENTOR(S) : Cecilia Munoz Calleja Page 1 of 1

It is certified that error appears in the above-identified patent and that said Letters Patent is hereby corrected as shown below:

Cover page under "References Cited" and "Other Publications" the Ghobrial et al. reference journal name "May Clinic Proceedings" corrected to read "Mayo Clinic Proceedings" (the Certificate of Correction issued May 1, 2012 is reinstated).

Column 17, line 1: "...an analyzed..." corrected to read "and analyzed" (the Certificate of Correction issued May 1, 2012 is reinstated).

Signed and Sealed this  
Sixth Day of November, 2012

David J. Kappos  
*Director of the United States Patent and Trademark Office*